(12) United States Patent
Babu et al.

(10) Patent No.: US 9,121,849 B2
(45) Date of Patent: *Sep. 1, 2015

(54) LATERAL FLOW ASSAYS

(71) Applicant: Rapid Pathogen Screening, Inc., Sarasota, FL (US)

(72) Inventors: Uma Mahesh Babu, Bradenton, FL (US); Robert P. Sambursky, Bradenton, FL (US); Robert W. VanDine, Montoursville, PA (US)

(73) Assignee: Rapid Pathogen Screening, Inc., Sarasota, FL (US)

( * ) Notice: Subject to any disclaimer, the term of this patent is extended or adjusted under 35 U.S.C. 154(b) by 106 days.

This patent is subject to a terminal disclaimer.

(21) Appl. No.: 13/790,229

(22) Filed: Mar. 8, 2013

(65) Prior Publication Data

US 2013/0210025 A1    Aug. 15, 2013

Related U.S. Application Data

(60) Division of application No. 12/957,683, filed on Dec. 1, 2010, and a continuation-in-part of application No. 12/502,626, filed on Jul. 14, 2009, now Pat. No. 8,669,052, and a continuation-in-part of application No. 12/481,631, filed on Jun. 10, 2009, now Pat. No. 8,470,608.

(60) Provisional application No. 61/266,641, filed on Dec. 4, 2009, provisional application No. 61/331,966, filed on May 6, 2010, provisional application No. 61/352,093, filed on Jun. 7, 2010, provisional application No. 61/392,981, filed on Oct. 14, 2010, provisional application No. 61/080,879, filed on Jul. 15, 2008, provisional application No. 61/098,935, filed on Sep. 22, 2008, provisional application No. 61/179,059, filed on May 18, 2009, provisional application No. 61/060,258, filed on Jun. 10, 2008.

(51) Int. Cl.
*C12Q 1/68* (2006.01)
*G01N 33/53* (2006.01)

(52) U.S. Cl.
CPC .......... *G01N 33/5308* (2013.01); *C12Q 1/6834* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 4,299,916 A | 11/1981 | Litman et al. | |
| 4,563,417 A | 1/1986 | Albarella et al. | |
| 4,859,612 A | 8/1989 | Cole et al. | |
| 4,956,302 A | 9/1990 | Gordon et al. | |
| 4,960,691 A | 10/1990 | Gordon et al. | |
| 4,960,692 A | 10/1990 | Lentrichia et al. | |
| 5,120,643 A | 6/1992 | Ching et al. | |
| 5,221,678 A | 6/1993 | Atkinson et al. | |
| 5,310,650 A | 5/1994 | McMahon et al. | |
| 5,312,921 A | 5/1994 | Glazer et al. | |
| 5,436,134 A | 7/1995 | Haugland et al. | |
| 5,496,562 A | 3/1996 | Burgoyne | |
| 5,637,469 A | 6/1997 | Wilding et al. | |
| 5,658,751 A | 8/1997 | Yue et al. | |
| 5,695,949 A | 12/1997 | Galen et al. | |
| 5,705,353 A | 1/1998 | Oh et al. | |
| 5,714,341 A | 2/1998 | Thieme et al. | |
| 5,756,126 A | 5/1998 | Burgoyne | |
| 5,763,162 A | 6/1998 | Glazer et al. | |
| 5,783,687 A | 7/1998 | Glazer et al. | |
| 5,807,527 A | 9/1998 | Burgoyne | |
| 5,824,268 A | 10/1998 | Bernstein et al. | |
| 5,863,740 A | 1/1999 | Kientsch-Engel et al. | |
| 5,877,028 A | 3/1999 | Chandler et al. | |
| 5,888,778 A | 3/1999 | Shuber | |
| 5,945,345 A | 8/1999 | Blatt et al. | |
| 5,972,386 A | 10/1999 | Burgoyne | |
| 5,985,327 A | 11/1999 | Burgoyne | |
| 5,989,813 A | 11/1999 | Gerdes | |
| 5,998,220 A | 12/1999 | Chandler | |
| 6,017,767 A | 1/2000 | Chandler | |
| 6,037,127 A * | 3/2000 | Ebersole et al. | ............. 435/6.19 |
| 6,046,058 A | 4/2000 | Sun | |

(Continued)

FOREIGN PATENT DOCUMENTS

DE    19622503         7/1998
EP    0306772 A1       3/1989

(Continued)

OTHER PUBLICATIONS

Cosa et al. "Photophysical Properties of Fluorescent DNA-dyes Bound to Single- and Double-Stranded DNA in Aqueous Buffered Solution." Photochemistry and Photobiology, 2001, 73(6): pp. 585-599.

(Continued)

*Primary Examiner* — Prabha Chunduru
(74) *Attorney, Agent, or Firm* — Brown & Michaels, PC

(57) ABSTRACT

Assays and methods including mobile tagged single stranded nucleic acid reagents pre-loaded on an analysis device, which are preferably tagged, but not labeled and are complementary to a strand (preferably the anti-sense strand in double stranded DNA targets) of the target nucleic acid. The assay also includes a running buffer that includes a dye or other detectable label that nonspecifically binds only to double stranded nucleic acids. In addition, the analysis device includes a detection zone including one or more test zones that have an immobilized tag that binds to the tag on the mobile nucleic acid reagent.

12 Claims, 10 Drawing Sheets

(56) References Cited

U.S. PATENT DOCUMENTS

| | | | |
|---|---|---|---|
| 6,054,272 A | 4/2000 | Glazer et al. | |
| 6,060,237 A | 5/2000 | Nygren et al. | |
| 6,087,184 A | 7/2000 | Magginetti et al. | |
| 6,106,779 A | 8/2000 | Buechler et al. | |
| 6,136,610 A | 10/2000 | Polito et al. | |
| 6,146,589 A | 11/2000 | Chandler | |
| 6,225,046 B1 | 5/2001 | Vesey et al. | |
| 6,277,652 B1 | 8/2001 | Jo et al. | |
| 6,284,550 B1 | 9/2001 | Carroll et al. | |
| 6,335,205 B1 | 1/2002 | Bausback | |
| 6,350,578 B1 | 2/2002 | Stark et al. | |
| 6,355,429 B1 | 3/2002 | Nygren et al. | |
| 6,358,752 B1 | 3/2002 | Durst et al. | |
| 6,514,773 B1 | 2/2003 | Klein et al. | |
| 6,555,390 B2 | 4/2003 | Chandler | |
| 6,566,101 B1 | 5/2003 | Shuber et al. | |
| 6,569,627 B2 | 5/2003 | Wittwer et al. | |
| 6,663,833 B1* | 12/2003 | Stave et al. | 422/81 |
| 6,783,938 B2 | 8/2004 | Nygren et al. | |
| 6,875,619 B2 | 4/2005 | Blackburn | |
| 6,902,900 B2 | 6/2005 | Davies et al. | |
| 7,189,522 B2 | 3/2007 | Esfandiari | |
| 7,267,992 B2 | 9/2007 | Goerlach-Graw et al. | |
| 7,309,611 B2 | 12/2007 | DiNello et al. | |
| 7,314,763 B2 | 1/2008 | Song et al. | |
| 7,341,837 B2 | 3/2008 | Lawton | |
| 7,354,614 B2 | 4/2008 | Quinlan et al. | |
| 7,371,582 B2 | 5/2008 | Nahm et al. | |
| 7,374,950 B2 | 5/2008 | Kang et al. | |
| 7,393,697 B2 | 7/2008 | Charlton | |
| 7,425,302 B2 | 9/2008 | Piasio et al. | |
| 7,459,314 B2 | 12/2008 | Guo et al. | |
| 7,566,573 B2 | 7/2009 | Carpenter et al. | |
| 7,723,124 B2 | 5/2010 | Aberl et al. | |
| 7,939,342 B2 | 5/2011 | Song et al. | |
| 8,470,608 B2* | 6/2013 | Babu et al. | 436/514 |
| 8,614,101 B2* | 12/2013 | VanDine et al. | 436/514 |
| 8,669,052 B2* | 3/2014 | Sambursky et al. | 435/6.1 |
| 2003/0073121 A1 | 4/2003 | Mendel-Hartvig et al. | |
| 2003/0104506 A1 | 6/2003 | Durst et al. | |
| 2003/0108940 A1 | 6/2003 | Inoko et al. | |
| 2003/0186463 A1 | 10/2003 | Hudak et al. | |
| 2003/0190681 A1 | 10/2003 | Shai | |
| 2004/0053255 A1 | 3/2004 | Lee et al. | |
| 2004/0072176 A1 | 4/2004 | Lee et al. | |
| 2004/0110167 A1 | 6/2004 | Gerdes et al. | |
| 2004/0152142 A1 | 8/2004 | Klepp et al. | |
| 2004/0156037 A1 | 8/2004 | Mawhirt et al. | |
| 2004/0241779 A1 | 12/2004 | Piasio et al. | |
| 2005/0032244 A1 | 2/2005 | Nie et al. | |
| 2005/0164305 A1 | 7/2005 | Golz et al. | |
| 2005/0181517 A1 | 8/2005 | Chandler et al. | |
| 2005/0227223 A1 | 10/2005 | Miyawaki | |
| 2005/0227275 A1 | 10/2005 | Jung et al. | |
| 2005/0239056 A1 | 10/2005 | Piasio et al. | |
| 2006/0003390 A1 | 1/2006 | Schaffler et al. | |
| 2006/0019406 A1 | 1/2006 | Wei et al. | |
| 2006/0057608 A1 | 3/2006 | Kaufman | |
| 2006/0110856 A1 | 5/2006 | Piasio et al. | |
| 2006/0160078 A1 | 7/2006 | Cardy et al. | |
| 2006/0172434 A1 | 8/2006 | Rowell | |
| 2006/0199278 A1 | 9/2006 | Leclipteux et al. | |
| 2006/0216704 A1 | 9/2006 | Newton et al. | |
| 2006/0223192 A1 | 10/2006 | Smith et al. | |
| 2006/0240569 A1 | 10/2006 | Goldenbaum et al. | |
| 2006/0263907 A1 | 11/2006 | Zweig | |
| 2007/0003992 A1 | 1/2007 | Pentyala | |
| 2007/0015290 A1 | 1/2007 | Raj | |
| 2007/0059682 A1 | 3/2007 | Aberl et al. | |
| 2007/0141564 A1 | 6/2007 | Aberl et al. | |
| 2007/0184506 A1 | 8/2007 | Klepp | |
| 2007/0202497 A1 | 8/2007 | Renuart et al. | |
| 2007/0224701 A1 | 9/2007 | Rosenstein | |
| 2007/0264629 A1 | 11/2007 | Holmes et al. | |
| 2008/0032319 A1 | 2/2008 | Nam | |
| 2008/0085525 A1 | 4/2008 | Van Herwijnen | |
| 2008/0102473 A1 | 5/2008 | Fouquet et al. | |
| 2008/0318341 A1 | 12/2008 | Esfandiari | |
| 2009/0011436 A1 | 1/2009 | Piasio et al. | |
| 2009/0047673 A1 | 2/2009 | Cary | |
| 2009/0155811 A1 | 6/2009 | Natan et al. | |
| 2009/0232702 A1 | 9/2009 | Wu et al. | |
| 2009/0291508 A1 | 11/2009 | Babu et al. | |
| 2009/0305231 A1 | 12/2009 | Weidemaier et al. | |
| 2010/0112725 A1 | 5/2010 | Babu et al. | |
| 2010/0143891 A1 | 6/2010 | Aberl et al. | |
| 2010/0143941 A1 | 6/2010 | Wu et al. | |
| 2010/0209297 A1 | 8/2010 | Raj et al. | |
| 2010/0291536 A1 | 11/2010 | Viljoen et al. | |

FOREIGN PATENT DOCUMENTS

| | | |
|---|---|---|
| EP | 0582231 A1 | 2/1994 |
| EP | 1489416 A1 | 12/2004 |
| GB | 1561042 | 2/1980 |
| WO | 9416108 A1 | 7/1994 |
| WO | 9960402 A1 | 11/1999 |
| WO | 0029112 A1 | 5/2000 |
| WO | 0204122 A2 | 1/2002 |
| WO | 03073817 A2 | 9/2003 |
| WO | 2007063326 A2 | 6/2007 |
| WO | 2007070117 A1 | 6/2007 |
| WO | 2007110779 A2 | 10/2007 |
| WO | 2007123507 A1 | 11/2007 |
| WO | 2008014709 A1 | 2/2008 |
| WO | 2009044167 A1 | 4/2009 |

OTHER PUBLICATIONS

Schweitzer and Scaiano. "Selective Binding and Local Photophysics of the Fluorescent Cyanine Dye Picogreen in Double-Stranded and Single-Stranded DNA." Phys. Chem. Chem. Phys., 2003, 5, pp. 4911-4917.

Nygren et al. "The Interactions Between the Fluorescent Dye Thiazole Orange and DNA." Biopolymers, vol. 46, 1998, pp. 39-51.

Morre et al. "Genotyping of *Chlamydia trachomatis* in Urine Specimens Will Facilitate Large Epidemiological Studies" Journal of Clinical Microbiology, vol. 36, No. 10 Oct. 1998, p. 3077-3078.

International Search Report and Written Opinion dated Jan. 22, 2010, International Application No. PCT/US2009/046848.

International Search Report and Written Opinion dated Feb. 18, 2010, International Application No. PCT/US2009/050645.

International Search Report and Written Opinion dated Mar. 12, 2010, International Application No. PCT/US2009/050653.

Barnard, et al., "Development of an Oligonucleotide-Based SNP Detection Method on Lateral Flow Strips Using Hexapet Tags," Point of Care, vol. 4, No. 3, pp. 108-118 (Sep. 2005).

Berezovski, et al., "Cell lysis inside the capillary facilitated by transverse diffusion of laminar flow profiles (TDLFP)," Anal Bioanal Chem (2007) 387:91-96.

Bruning et al., "A rapid chromatographic strip test for the pen-side diagnosis of rinderpest virus," Journal of Virological Methods 81 (1999) 143-154.

Chieux V, et al., "The MxA protein levels in whole blood lysates of patients with various viral infections," Journal of Virological Methods 70 (1998) 183-191.

Choi, et al., "A rapid, simple measurement of human albumin in whole blood using a fluorescence immunoassay (I)," Clinica Chimica Acta 339 (2004) 147-156.

Karle, et al., "Application of FTA-based Technology for Sample Collection, Transport, Purification, and Storage of PCR-ready Plant DNA" (Nov. 2003).

O'Mahony, et al., "Integration of Bacteria Capture via Filtration and in Situ Lysis for Recovery of Plasmid DNA under Industry-Compatible Conditions," Biotechnol. Prog. 2007, 23, 895-903.

Parida M.M., "Rapid and real-time detection technologies for emerging viruses of biomedical importance," J. Biosci. 33 (4), Nov. 2008, 617-628.

Sambursky, "510-K Summary of Safety and Effectiveness" (Sep. 14, 2005).

(56) References Cited

OTHER PUBLICATIONS

Sambursky et al., "The RPS Adeno Detector for Diagnosing Adenoviral Conjunctivitis," Ophthalmology 2006; 113:1758-1764.
Uchio, et al., "Rapid Diagnosis of Adenoviral Conjunctivitis on Conjunctival Swabs by 10-Minute Immunochromatography," Ophthalmology 1997; 104:1294-1299.
Udeh et al., "Cost Effectiveness of a Point-of-Care Test for Adenoviral Conjunctivitis," Am J Med Sci 2008; 336 (3):254-264.
"FTA Nucleic Acid Collection, Storage and Purification," Whatman website, http://whatman.com/products.aspx?PID=108, at least as early as Mar. 2008.
International Search Report and Written Opinion for International Application No. PCT/US2010/058822 Issued on Aug. 25, 2011.
Extended European Search Report for EPO Application No. 09798690.5. Issued on Oct. 24, 2012.
Rule et al. "Rapid Method for Visual Identification of Specific DNA Sequences based on DNA-Tagged Liposomes." Clinical Chemistry. vol. 42, No. 8. pp. 1206-1209. 1996.
Carter et al. "Lateral Flow Microarrays: A Novel Platform for Rapid Nucleic Acid Detection Based on Miniaturized Lateral Flow Chromatography" vol. 35, No. 10. 2007.
Dineva et al. "Simultaneous Visual Detection of Multiple Viral Amplicons by Dipstick Assay" vol. 43, No. 8. pp. 4015-4021. 2005.
Kalogianni, D.P. et al., "Dry Reagent Dipstick Test Combined With 23S rRNA PCR for Molecular Diagnosis of Bacterial Infection in Arthroplasty" Anal. Biochem., vol. 361, pp. 169-175 (2007).
Robert, P-Y. et al. "Multiplex Detection of Herpesviruses in Tear Fluid Using the "Stair Primers" PCR Method: Prospective Study of 93 Patients" J. Med. Virol., vol. 66, pp. 506-511 (2002).
Stender, H. et al. "PNA for Rapid Microbiology." J. Microbiol. Meth., vol. 48, pp. 1-17 (2002).

\* cited by examiner

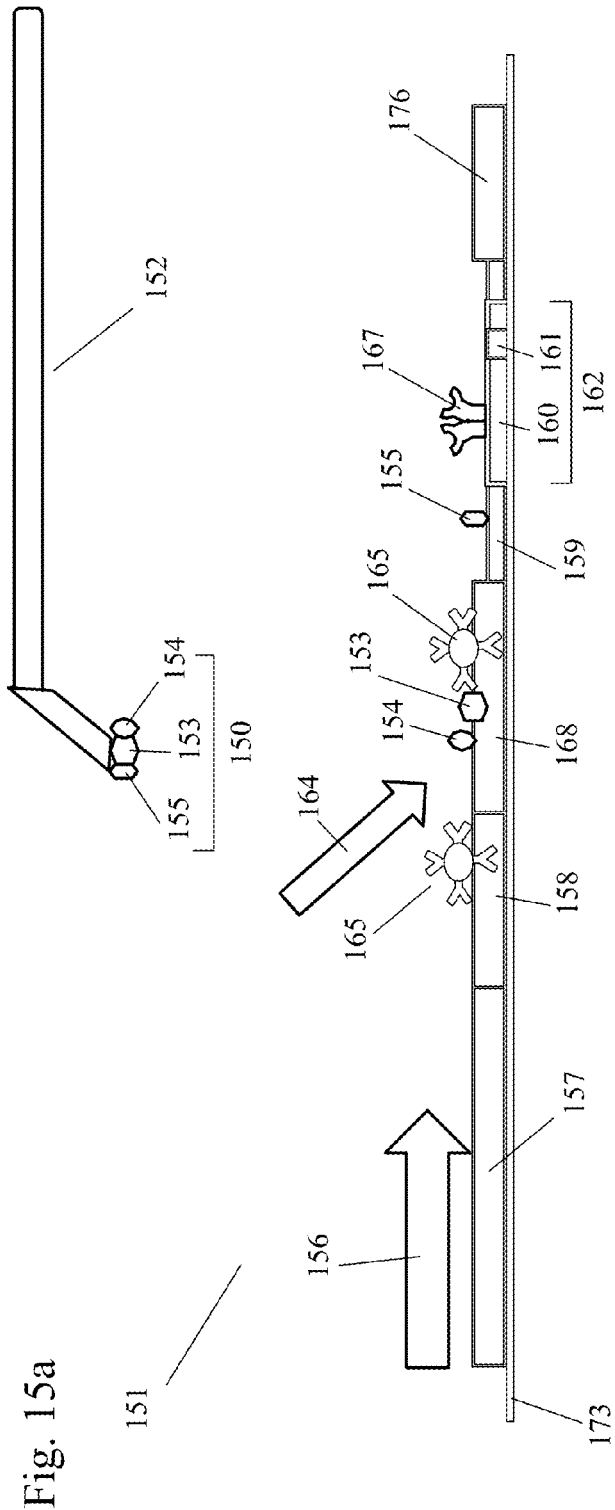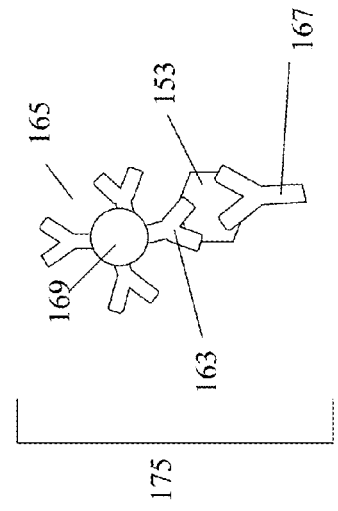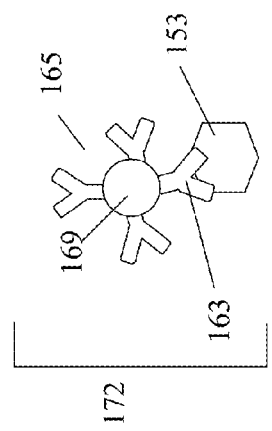

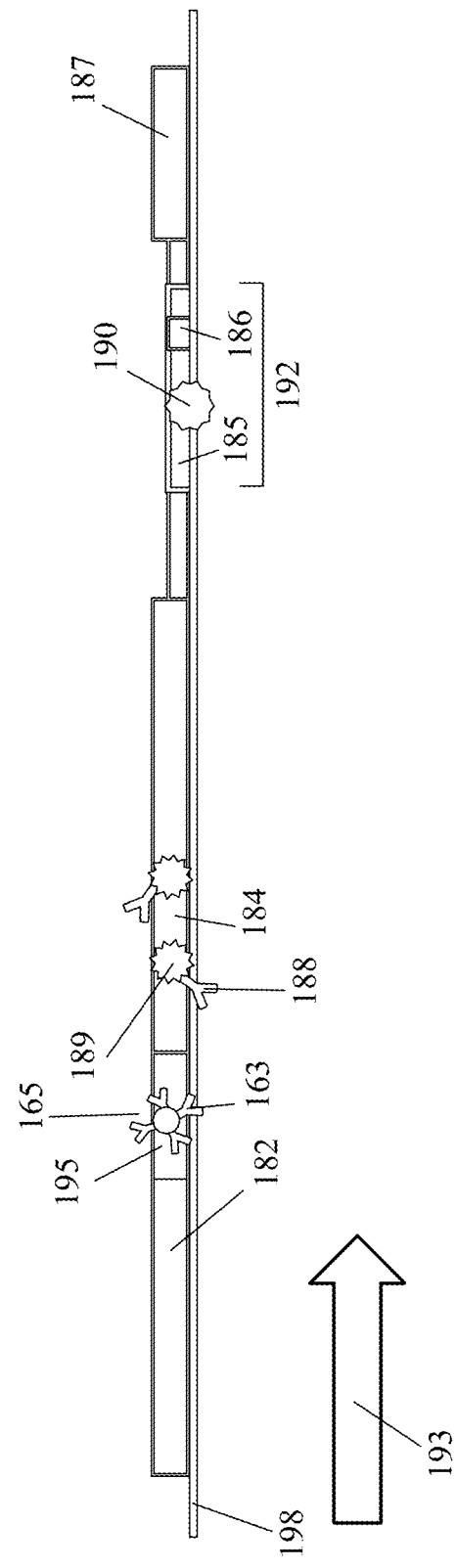
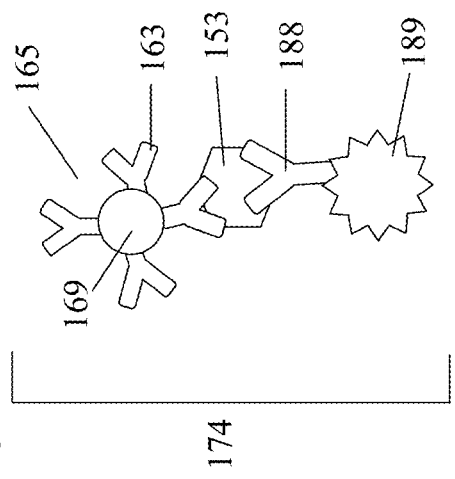
Fig. 16a
Fig. 16b

LATERAL FLOW ASSAYS

REFERENCE TO RELATED APPLICATIONS

This is a divisional patent application of co-pending application Ser. No. 12/957,683, filed Dec. 1, 2010, entitled "LATERAL FLOW ASSAYS", which claims one or more inventions which were disclosed in Provisional Application No. 61/266,641, filed Dec. 4, 2009, entitled "LATERAL FLOW NUCLEIC ACID DETECTOR", Provisional Application No. 61/331,966, filed May 6, 2010, entitled "MULTIPLANAR LATERAL FLOW ASSAY WITH SAMPLE COMPRESSOR", Provisional Application No. 61/352,093, filed Jun. 7, 2010, entitled "LATERAL FLOW ASSAYS", and Provisional Application No. 61/392,981, filed Oct. 14, 2010, entitled "MULTIPLANAR LATERAL FLOW ASSAY WITH SAMPLE COMPRESSOR".

This application is also a continuation-in-part application of application Ser. No. 12/502,626, filed Jul. 14, 2009, entitled "LATERAL FLOW NUCLEIC ACID DETECTOR", which claims one or more inventions which were disclosed in Provisional Application No. 61/080,879, filed Jul. 15, 2008, entitled "LATERAL FLOW NUCLEIC ACID DETECTOR", Provisional Application No. 61/098,935, filed Sep. 22, 2008, entitled "IN SITU LYSIS OF CELLS IN LATERAL FLOW IMMUNOASSAYS", and Provisional Application No. 61/179,059, filed May 18, 2009, entitled "METHOD AND DEVICE FOR COMBINED DETECTION OF VIRAL AND BACTERIAL INFECTIONS" and is a continuation-in-part application of application Ser. No. 12/481,631, filed Jun. 10, 2009, entitled "COMBINED VISUAL/FLUORESCENCE ANALYTE DETECTION TEST", which claimed priority from Provisional Application No. 61/060,258, filed Jun. 10, 2008, entitled "COMBINED VISUAL/FLUORESCENCE ANALYTE DETECTION TEST".

The benefit under 35 USC §119(e) of the United States provisional applications is hereby claimed, and the aforementioned applications are hereby incorporated herein by reference.

BACKGROUND OF THE INVENTION

1. Field of the Invention

The invention pertains to the field of lateral flow assays for the detection of analytes.

2. Description of Related Art

Lateral flow assays are a subset of assays combining various reagents and process steps in one assay strip, thus providing a sensitive and rapid means for the detection of target molecules. Lateral flow immunoassays are available for a wide area of target analytes and can be designed for sandwich or competitive test principles. Generally high molecular weight analytes with several epitopes are analyzed in a sandwich format whereas small molecules representing only one epitope are detected by means of a competitive assay. The first tests were made for human chorionic gonadotropin (hCG). Today, there are commercially available tests for monitoring ovulation, detecting infectious disease organisms, analyzing drugs of abuse, and measuring other analytes important to human physiology. Products have also been introduced for veterinary testing, environmental testing, and product monitoring.

SUMMARY OF THE INVENTION

Embodiments of the present invention include assays where the analyte (target) to be detected does not bind directly to an immobilized binding partner in the test zone of a test strip. Instead, the analyte preferably interacts with one or more analyte binding partners in other zones (including the buffer, in some embodiments) on the strip. At least one of the analyte binding partners includes a first tag that forms a complex with a second immobilized tag in the test zone.

In some preferred embodiments, the assays and methods do not use any microspheres, beads, or suspensions (such as colloidal gold or colored latex beads). Instead, the visualization at the test and control lines is due to the acquisition and accumulation of soluble dyes delivered to the detection zone.

In some preferred embodiments, a binding assay of the present invention preferably includes a mobile tagged single stranded nucleic acid reagent pre-loaded on an analysis device. The mobile single stranded nucleic acid reagent is preferably tagged, but not labeled. The mobile tagged singled stranded nucleic acid reagent is complementary to a strand (preferably the anti-sense strand in double stranded DNA targets) of the target nucleic acid. The assay also preferably includes pre-loaded lysis agents and/or nucleic acid denaturants, which lyse the components of the sample, and denature any double stranded target nucleic acid into single strands. The assay is applicable to both DNA and RNA test samples. The assay is also applicable regardless of whether the test sample is double stranded in its native form or single stranded in its native form. The assay also includes a running buffer that includes a dye or other label that nonspecifically binds double stranded nucleic acids. The dye or label is preferably visible to the naked eye and/or fluorescent, but may be detectable by other known methods. In addition, the analysis device includes a detection zone including one or more test zones that have an immobilized tag that binds to the tag on the mobile single stranded nucleic acid reagent.

In one preferred method of the present invention, the sample is preferably lysed by one or more lysis agents to make the nucleic acid in the sample accessible to the components of the assay. Pathogenic as well as non-pathogenic organisms produce enzymes which may be present in the sample and beneficially aid in lysis. In embodiments where the nucleic acid is double stranded, the lysis agent includes one or more nucleic acid denaturants that denatures the nucleic acid into single strands. The lysis agents are preferably located in a lysis zone on a chromatographic test strip. In other embodiments, the lysing is performed external to the device or included in the running buffer. When the mobile tagged single stranded nucleic acid reagent encounters the single stranded target nucleic acid, a double stranded complex between the mobile tagged single stranded nucleic acid reagent and the single stranded target nucleic acid forms. If the target nucleic acid is not in the sample, no double stranded complex will form. A mobile label in the running buffer or embedded either upstream of the application zone, in the application zone, or downstream to the application zone, binds to the double stranded nucleic acid complex, forming a labeled duplex complex. When the labeled duplex complex reaches an immobilized test line of the detection zone, the tag on the mobile tagged single stranded nucleic acid reagent binds to a tag immobilized on the test line. When the test is positive (target nucleic acid is in the sample), the final complex is labeled with the label (for example, a dye), and the test line is detectable, for example it is visible to the naked eye and/or under fluorescence. When the test is negative (no target nucleic acid in the sample), the mobile tagged single stranded nucleic acid reagent remains single stranded. The immobilized tag still binds to the tag on the mobile tagged single stranded nucleic acid reagent when the test is negative. However, the resulting complex is not labeled and nothing is detectable at the test line.

A test kit for detection of at least one target nucleic acid in a sample includes a test strip including at least one detection zone that includes at least one test zone. The test strip also includes a sample application zone for applying the sample to the test strip and at least one mobile tagged nucleic acid reagent including a plurality of nucleic acids complementary to a first portion of a sequence of the target nucleic acid and at least one tag portion but not including a label. The mobile tagged nucleic acid reagent is loaded in a reagent zone. The test strip preferably also includes at least one lysis agent that processes the sample such that the target nucleic acid can bind to the mobile tagged nucleic acid reagent when the target nucleic acid encounters the mobile tagged nucleic acid reagent. The lysis agent is loaded in a lysis zone or is in the buffer. The test strip also includes at least one immobilized tag that is immobilized in a test zone of the assay, which binds to the tag portion of the mobile tagged nucleic acid reagent. The test kit also includes a running buffer including at least one detectable label that binds only to double stranded nucleic acids. The double stranded nucleic acid to which the detectable label binds can be PNA:DNA, DNA:DNA, PNA:RNA, RNA:DNA or RNA:RNA.

In other preferred embodiments, a binding assay preferably includes a first analyte binding partner with a detectable label (the labeled conjugate) and a second analyte binding partner that is tagged but not labelled. The assay also includes a detection zone, which includes an immobilized tag that forms a complex with the tag on the second binding partner. In preferred embodiments, a "full sandwich" is preferably formed between the first analyte binding partner, the analyte, and the second analyte binding partner before the complex reaches the detection zone.

BRIEF DESCRIPTION OF THE DRAWINGS

FIG. 15a shows a test strip and sample collector.

FIG. 15b shows a "half" sandwich that forms between the analyte and the labeled conjugate.

FIG. 15c shows a "full" sandwich that forms at the test line between the analyte, the labeled conjugate, and an immobilized binding partner.

FIG. 16a shows a lateral flow test strip in an embodiment of the present invention.

FIG. 16b shows a "full" sandwich, which preferably forms before reaching the test line, between the analyte, the labeled conjugate, and a second tagged mobile binding partner.

DETAILED DESCRIPTION OF THE INVENTION

Figure 1:
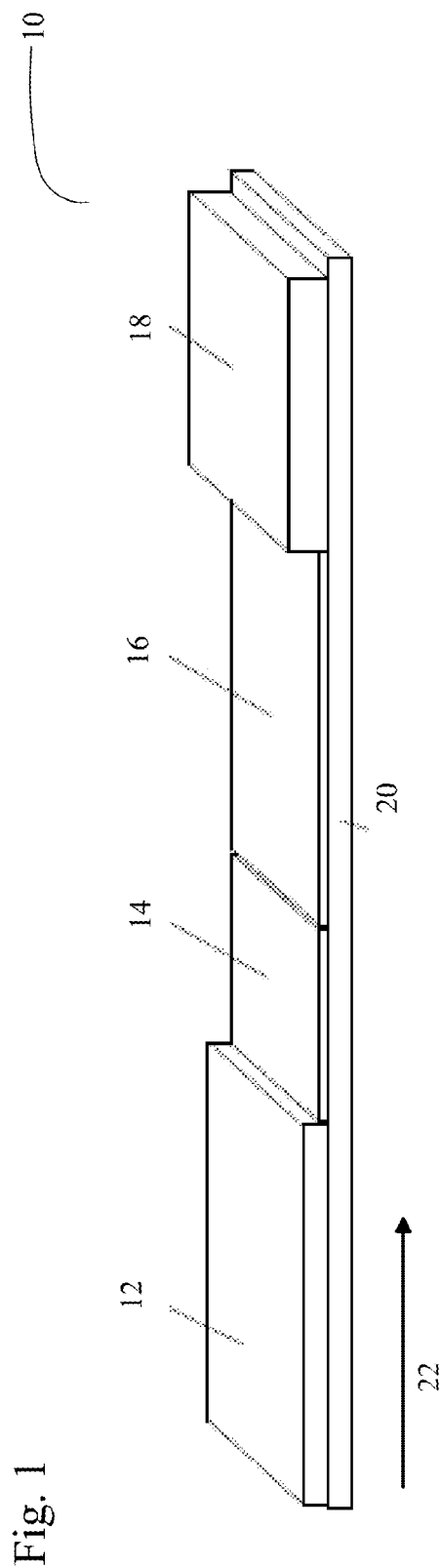
FIG. 1 shows a schematic side view of a test strip for a lateral flow binding assay in an embodiment of the present invention.

Rapid point-of-care analysis is becoming increasingly important in the screening and/or diagnosis and treatment of various viral and other pathogenic microbiological agents. Prior art point-of-care tests, such as lateral flow immunochromatography tests, are immunoassays involving an antibody and its antigen. Prior art sandwich immunoassays included at least one binding partner for the analyte immobilized at the test line in the detection zone of the test strip. Binding assays in some formats operate on the basis of ligands and receptors and their associated binding constants.

The inherent deficiencies in the associations between antibodies and their antigens are well known in the art in that ligand-receptor binding assays are prone to degrade with temperature cycling and heat stress while in storage, and interferences often occur from components in the sample matrix, causing non-specific binding during the assay and leading to false results. These inherent limitations do not provide sufficient specificity in the ligand-receptor interaction for reliable assay results. Ligand-receptor binding provides the above-mentioned specificity and limitations to a protein antigen target but not to a nucleic acid sequence coding for the protein.

The present invention includes assays where the analyte to be tested for does not bind directly to an immobilized binding partner in the test zone of a test strip. Instead, the analyte preferably interacts with one or more analyte binding partners in other zones (including the buffer, in some embodiments) on the strip. At least one of the analyte binding partners preferably includes a first tag that forms a complex with a second immobilized tag in the test zone.

The assays described herein are preferably "point-of-care assays", which, as defined herein, include both lateral flow assays and flow through assays. These point-of-care assays may be run and results read within a matter of minutes to a few hours after the sample is obtained, but the assays may alternatively be run at a later time such as up to 24 to 48 hours after obtaining the sample. The analytical tests discussed herein preferably permit a result while the patient is still being examined by the practitioner. In a preferred embodiment, the test result is obtained in under 10 minutes after applying the sample to the device, and it is preferably read approximately 10 minutes after applying the sample. In samples that are highly positive, a read-out of the test zone (preferably a test line) is visible within 1 to 5 minutes. The tests are also much more heat stable and easier to manufacture than prior art point-of-care diagnostic tests.

The flow of the transport liquid in the detector may be gravity-dependent or as a result of capillary action or surface tension. The transport liquid may be applied by dipping the test strip in the transport liquid, injecting liquid onto the test strip, or the transport liquid may be contained in a test housing for the test strip.

The detectors of the present invention may be uniplanar with a single sheet on a test strip for the detection zone. Alternatively, the detectors may be multiplanar with multiple detection zones on multiple sheets in fluid communication for simultaneous assays for the same or different target analytes from the same or different samples.

A sample for testing in the present invention may be any sample expected to potentially include a target nucleic acid or other analyte including, but not limited to, saliva, nasopharyngeal secretions, mucus, tissue, blood, urine, tears, vaginal or penal fluid, cerebrospinal fluid, skin ulcerations, an environmental water sample, food sources, inanimate hard surfaces, and a soil sample.

Some preferred materials and membranes for the test strip include, but are not limited to, Polyethylene terephthalate (PET) fibers, such as Dacron® fibers, nitrocellulose, polyester, nylon, cellulose acetate, polypropylene, glass fibers, and combinations of these materials and their backings. The characteristics of the fleeces and membranes depend upon the types of materials used for a particular region or zone of the test strip or collection device. As described herein, materials that allow reagents (including those in the reagent zone, labeled conjugate zone, lysis zone, sample application zone, or any of the other zones or lines described herein) to be mobile and travel with the elution medium include fleece materials or fibers, where the binding is not specific or permanent, so that the analyte and reagents may be released when they encounter the elution medium or with large sample volume. Some of these materials include, but are not limited to, Polyethylene terephthalate (PET) fibers, such as Dacron® fibers, nylon fibers, polyester fibers, cellulose acetate fibers, polypropylene fibers, glass fibers, and other fabrics and meshes. In contrast, materials that immobilize reagents in a particular zone (including, for example, the reagents immobilized on the test line and control line of the detection zone) include, but are not limited to, nitrocellulose, hydrogel, and nylon fibers chemically treated such that individual fibers in the nylon mesh bind permanently to reagents such as proteins. Some methods for manufacturing different portions of the strip include, but are not limited to, striping, spraying, soaking and drying materials onto the strip.

A lateral flow nucleic acid detector of the present invention preferably detects nucleic acids in a sample without utilizing the polymerase chain reaction or other amplification steps designed to enhance sensitivity for the target nucleic acid. The methods and detectors described herein are able to detect the target nucleic acids without amplifying the target nucleic acids. However, if the test analyte is already amplified, the amplified sample can still be used as a sample in the embodiments described herein. In some embodiments, the detected nucleic acids are also quantified. Some examples of how the nucleic acids may be quantified include, but are not limited to, quantification through visual gradations of the line intensity or through the use of an electronic optical reader.

Viruses and organisms that contain DNA or RNA can be detected through the usage of their nucleic acid as the target. Certain specific single stranded sequences of nucleic acids bind the target nucleic acid by hybridization. This binding always results in the formation of double stranded nucleic acid sequences.

There are specific labels or dyes which bind only to double stranded nucleic acids and not single strand nucleic acid sequences. Peptide nucleic acids (PNAs) bind to their complementary ribo or deoxyribo nucleic acid sequences under a wide range of pH and salt concentrations. PNA binding is stronger than the RNA or DNA binding and PNAs are resistant to mammalian nucleases and are generally more stable.

In preferred embodiments, there is a reagent zone that includes one or more mobile tagged reagent nucleic acids, with a sequence complementary to a target nucleic acid sequence. In some embodiments, the mobile tagged reagent nucleic acids are Peptide Nucleic Acid (PNA) sequences. In some embodiments, the reagent nucleic acids are tagged with biotin. The reagent nucleic acids do not include a detectable label. Instead, a detectable label (for example, a dye) that binds only to double stranded nucleic acids is included in the running buffer or elsewhere (for example, somewhere on the test strip). The label is preferably detectable visibly and/or by fluorescence, but any form of detection known in the art may be used, depending upon the label chosen. Since the label binds only to double stranded nucleic acids, the tag at the test zone does not bind directly to the analyte (the target nucleic acid). Note that the complex between the tag on the reagent nucleic acids and the immobilized tag in the detection zone occurs regardless of whether or not the analyte is present. However, the complex is only detectable when the analyte is present and the reagent nucleic acids have bound to the analyte nucleic acid.

While any label that nonspecifically binds only to double stranded nucleic acid could be used, some examples include, but are not limited to, SYBR® green dye, PicoGreen® reagents or ethidium bromide. The device also preferably includes a lysis/denaturant zone including a lysis agent that lyses the sample components, and, in embodiments where the target nucleic acid is a double stranded nucleic acid, preferably also denatures any double stranded nucleic acid in the sample. Pathogenic as well as non-pathogenic organisms produce enzymes which may be present in the sample and beneficially aid in lysis. The detection zone includes an immobile tag that binds to the tag portion of the reagent nucleic acids. In embodiments where the tag on the reagent nucleic acids is biotin, the immobilized tag in the detection zone is preferably avidin, neutravidin, or streptavidin.

The term "label" as used herein refers to any atom, atoms, molecule, or molecules, such as a phosphorescent or fluorescent tag, used to provide a detectable and preferably quantifiable signal. Methods of detection of the label include, but are not limited to, visible detection, fluorescence, chemiluminescence, radioactivity, colorimetry, gravimetry, X-ray diffraction, X-ray absorption, magnetism, fluorescent resonant emissions, and enzymatic activity. Visible spectrum test lines may be interpreted by a spectrometer to yield quantified test results.

Qualitative interpretation is performed visually by observing the test line intensity and hue. In an example where a visual red dye is used as the label, when the concentration of the analyte is equal or slightly above the lower limit of detection, the test line can be seen faintly and the hue is pink. As the concentration of the analyte is increased, the test line intensity correspondingly increases and the hue shifts from pink to bright red. Other colors can also be employed and are not limited to pink or red. A combination of colors can be used such that the color and/or hue changes with a increased intensity (e.g. changing from pink to purple). A quantitative interpretation is developed using a spectrometer operating in the visible spectrum. Either an absorption or a reflectance measurement may be used in the visible spectrum to develop the quantification of the test line. First a set of characterized concentrations of the analyte are developed. Each of the concentrations is applied to the sample application zone and the test is developed. The spectrometer is used to measure either the absorption or the reflectance of the test line. A standard curve is calculated from the measured values of the spectrometer. The standard curve is normally linear. In other embodiments, if fluorescent tags are used, a similar set of known concentrations of the analyte may be developed. An unknown concentration of the analyte tested and quantified by the spectrometer yields a value that, when plotted on the standard curve, can be correlated to a concentration of analyte.

In a method of the present invention, a sample is added to the sample application zone of a chromatographic test strip. The sample preferably encounters a lysis zone on the test strip, where the sample is lysed and denatured in situ. In other embodiments, the sample is lysed and denatured prior to being transferred to the test strip. For example, the sample may be transferred to a solution which contains lysis and denaturing agents. In other examples, the sample collection device may include pre-loaded lysis and denaturing agents that lyse and denature the sample prior to its transfer to the test strip.

If the target nucleic acid is in the sample, the now available single stranded target nucleic acid then encounters the tagged reagent nucleic acid, and the two single stranded sequences form a double stranded complex due to complementary base pairing. The double stranded complex binds to the dye/label in the running buffer or elsewhere, and travels to the detection zone, where the tag on the reagent nucleic acid binds to the immobile tag in the detection zone. While this binding will occur whether or not the target nucleic acid is in the sample, the resulting complex will only be detectable (for example, visibly or fluorescently) if the label in the running buffer or elsewhere has also bound to the complex, which will only occur if the tagged reagent nucleic acid has bound to the target nucleic acid.

In a preferred embodiment, one or more specific tagged nucleic acid partner PNA sequences complementary to a target RNA or DNA of a virus or another organism is embedded into a reagent zone of a lateral flow strip. Lateral flow devices are known, and are described in, e.g., U.S. Published Patent Application Nos. 2005/0175992 and 2007/0059682. The contents of both of these applications are incorporated herein by reference. Other lateral flow devices known in the art could alternatively be used with the systems and methods of the present invention.

The PNAs are preferably also synthesized with a biotin "tail". The test sample containing the target RNA/DNA is added to the strip on a sample application zone. Commercially available lysis agents and/or denaturants (for example, DNAZol® reagents) are preferably impregnated or embedded in the sample application zone. Thus, the virus or other organism is lysed in situ and hybridizes with the biotinylated PNAs. The running buffer containing double strand nucleic acid binding dyes (for example, SYBR® Green dye, PicoGreen® reagents or Ethidium Bromide dye) binds to the double strand sequences of the tagged nucleic acid partner PNA: target nucleic acid sequence. These dyes are preferably visible as well as fluorescent. The running buffer transports these complexes to a detection zone where immobilized avidin binds to the biotinylated PNAs in the "dyed duplex". The dyed duplex then accumulates in the detection zone. Under their specific excitation wavelength, there is an emission of fluorescence which can be visually observed or "read" by a spectrometer. There are dyes that can become turbid in the presence of certain salts such as magnesium pyrophosphate and one can ascertain the turbidity also at the test line.

These embodiments eliminate the need for detectable (e.g. by the naked eye or by fluorescence) labels on the tagged nucleic acid partner and thus has considerable advantages in manufacturing as well in the stability of the test.

Regarding materials and compositions incorporated into the running buffer or impregnated or embedded into the test strip in the reagent zone and/or the lysis zone, any material and composition combinations capable of lysing the sample (and denaturing the nucleic acids, if necessary) without destroying the target nucleic acids could be used in the present invention. There are commercially available lysis agents (for example, DNAzol® reagents, Life Technologies, Carlsbad, Calif.) that could be impregnated or embedded into the strip material. Some other examples of reagents that would denature the nucleic acids include, but are not limited to, uric acid, high salt concentration solutions, high pH solutions, certain detergents, and any combination thereof. There are also commercially available membranes or lattices where lysis agents are already impregnated or embedded. Although long term storage is not necessary in all embodiments of the present invention, there are also known mediums capable of storing DNA, for example those disclosed in U.S. Pat. Nos. 5,496,562, 5,756,126, 5,807,527, 5,972,386, and 5,985,327, herein incorporated by reference. One example of a medium that contains chemicals that lyse samples, denature proteins and protect nucleic acids from degradation are Whatman FTA 25 cards (Whatman, Kent, UK). By using these types of pads, manufacturing steps can be further reduced. Other materials and compositions could be used in the present invention to impregnate and maintain the mobile tagged nucleic acids in the reagent zone.

Where each zone is on the strip may vary. For example, the reagent zone (containing the mobile tagged nucleic acid reagents) may be located upstream of the sample application zone, overlapping the sample application zone or downstream of the sample application zone.

Similarly, the lysis zone may overlap the sample application zone or be either upstream or downstream of the sample application zone. In other embodiments, the lysis agent may be incorporated into the sample collector device. In these embodiments, the sample collector device is preferably separate from the lateral flow strip, but it may alternatively be integral with the lateral flow strip. These embodiments are particularly useful when it is unnecessary for the sample collector device to be biocompatible or sterilized. For example, the lysis agent could be on the sample collection device when testing samples which are exudates such as sputum, urine or blood, cultures, inanimate surfaces, ecological samples or agricultural samples.

The reagent zone may also be upstream, downstream or overlapping the lysis zone, as long as the mobile tagged nucleic acid reagents encounter the sample at some point during or after it is being lysed so that a double stranded complex can form between the mobile tagged nucleic acid reagents and the target nucleic acids.

In some preferred embodiments, there are additional compositions in the running buffer that neutralize the lysis agent such that it does not destroy the mobile tagged nucleic acids or other components of the assay. Some examples, depending on the lysis agent used, include, but are not limited to, strong buffers that neutralize high pH, hypotonic solutions to lower hypertonicity, diluting agents to dilute the detergents and denaturants, or chelating agents that bind to high salt solutions.

One advantage of embodiments of the present invention includes increased heat stability of lateral flow assays. The reagents, including the nucleic acids and the running buffer, are heat stable. Another advantage when using PNAs as the mobile tagged nucleic acid reagents is increased sensitivity relative to prior art assays. Since the backbone of PNAs contain no charged phosphate groups, the binding between PNA/DNA strands is stronger than between DNA/DNA strands due to the lack of electrostatic repulsion. Similarly, PNA/RNA binding is stronger than DNA/RNA. Since the present invention does not use PCR, heat cycling of RT-PCR DNA analysis is eliminated. However, the products from RT-PCT can be used as the starting sample in the assays and methods described herein.

In preferred embodiments, the sample application zone is coated with two compositions. The first is a composition that lyses components of the sample. The lysis agents may be commercially available lysis agents such as DNAZole or others known in the art. Some other examples include, but are not limited to, strong buffers or acidic solutions to neutralize the pH in a hypotonic solution. Some other examples of reagents that would denature the nucleic acids include, but are not limited to, uric acid, high salt concentration solutions, high pH solutions, certain detergents, and any combination thereof. In embodiments where the target nucleic acid is double stranded DNA or double stranded RNA in the sample, the first composition also denatures the target DNA or RNA into single strands. The second composition is a cocktail of Peptide Nucleic Acid sequences selected to bind to the antisense (complementary) portions of the single stranded DNA or RNA. The PNAs are preferably tagged with biotin. The lysis composition and PNA are both mobile reagents. When at least a portion of the sample is transferred to the sample application zone of the test strip, a first complex is formed between the target nucleic acid and its complementary PNAs. A running buffer label that nonspecifically binds to double stranded nucleic acid is applied to the test strip. The label binds to any double stranded nucleic acids formed by the complementary binding of the target nucleic acid and the tagged PNAs, forming a second complex. In some embodiments, SYBR® green dye is used as the label. The detection zone is impregnated with a tag complementary to the tag on the PNAs. In embodiments where biotin is used, avidin, neutravidin or streptavidin is the immobilized tag in the detection zone. The immobilized avidin binds to the biotin tag on the PNA in the second complex, forming a third complex. The visual/fluorescent dye can then be visualized by the naked eye or by fluorescence. Presence of the signal indicates that the target nucleic acid is in the sample. If there is no target nucleic acid present, the immobilized avidin still binds to the biotin tag on the PNA, but the single stranded PNAs are not bound to the dye and thus there is nothing detected in the detection zone by the naked eye or fluorescence.

Note that the location of sample loading, lysis agent preloading and reagent zone reagent pre-loading depends on the conditions of the assay, and may be varied as long as the sample encounters the mobile tagged nucleic acid reagents on the test strip such that the target nucleic acid sequence can bind to the complementary nucleic acid sequence of the mobile tagged nucleic acid reagents. For example, the sample may be added directly onto the mobile tagged nucleic acid reagents and other embedded materials or downstream or upstream of the mobile tagged nucleic acid reagents and the embedded materials. Similarly, the sample may be added directly onto the lysis agents in the lysis zone or downstream or upstream of the lysis agents. The reagent zone may be upstream of the lysis zone, as long as the mobile tagged nucleic acid reagents are able to access and bind to a single stranded version of the target nucleic acid and also bind to the double stranded binding label in the running buffer before reaching or when simultaneously reaching the test line of the detection zone.

Some embodiments also include a control zone, waste zone, or absorbent pad on the test strip.

The detector may be used to detect a target nucleic acid sequence associated with any target virus, bacterium, fungus, protozoa, other pathogens, allergens, any genetic deficiency, or any other target nucleic acid in a sample. Other target nucleic acids include, but are not limited to, those that code for tumor markers (oncogenes), cardiac markers (for example, myoglobin, troponin, creatine kinase, MMP-9, C-reactive protein) inflammatory markers (such as cytokines, lymphokines, chemokines, cellular signaling factors, chemoattractants, metalloproteinases, interferons, MxA, and growth factors), hormones, and tissue typing. The target nucleic acid may be any nucleic acid including, but not limited to, DNA, an oligonucleotide, messenger RNA, or any other type of RNA. In embodiments where the nucleic acid is naturally double stranded in the sample, the target nucleic acid is denatured and separated into single-stranded strands so that it can bind with its complementary tagged nucleic acid reagent.

The present invention is particularly useful for detecting single stranded viruses including, but not limited to, single stranded DNA viruses (for example, Parvoviruses including, but not limited to, fifth disease), (+)single stranded RNA viruses (for example SARS virus, hepatitis C virus, yellow fever virus, Dengue fever virus, West Nile Virus, Japanese encephalitis virus, other Flaviviruses, rubella virus, chikengunya virus, other Togaviruses, and Picornaviruses including Hepatitis A virus, enteroviruses, rhinoviruses, poliovirus, Norwalk virus, and foot-and-mouth virus), (−)single stranded RNA viruses (for example Orthomyxoviruses and Rhabdoviruses including Ebola virus, Marburg virus, influenza virus, avian influenza, swine influenza, measles, mumps and rabies) and single stranded RNA-RT viruses (for example, retroviruses including, but not limited to, HIV). In other preferred embodiments, the invention detects double stranded viral targets, including, but not limited to, double stranded DNA viruses (for example, Adenoviruses, Herpesviruses, and Poxviruses), double stranded RNA viruses (for example, Reoviruses), and double stranded DNA-RT viruses (for example, Hepadnaviruses). In embodiments detecting viruses that have double-stranded nucleic acid in the sample, the DNA or RNA is denatured by a lysis agent in a lysis zone such that it becomes single stranded and accessible to the tagged binding partner nucleic acid sequence. Other preferred target nucleic acid sequences are from bacteria. One example is nucleic acid sequences from *Coxiella burnetii* (which causes Q fever).

The early diagnosis and treatment of sexually transmitted diseases is extremely important for patient health and to avoid further spread of the disease. Some examples of prevalent sexually transmitted diseases include, but are not limited to HIV, genital herpes, Chlamydia, gonorrhea, syphilis, human papillomavirus (HPV), hepatitis B (HBV), Trichomoniasis and bacterial vaginosis. Unfortunately, there is currently no rapid point of care test available that is sufficiently heat stable to be used to diagnose these diseases in the hotter areas of the world, such as Africa. Instead, all of the current tests use antibodies, which are naturally occurring and are prone to degrade with temperature cycling and heat stress while in storage. The present invention does not rely on antibodies, and instead is able to use synthetic reagents. Thus, the device is much more heat stable and would be particularly useful in detecting sexually transmitted diseases in warm climates.

The nucleic acid sequences used to detect the target nucleic acid sequences can be of any length such that they are specific to the target of interest. In preferred embodiments, the sequences are approximately 10 to 25 nucleotides long, however, longer or shorter sequences are possible, as long as they provide the requisite specificity and do not otherwise interfere with the assay. In some preferred embodiments, the sequences are around 15 to 17 nucleotides long. If peptide nucleic acid sequences (PNAs) are being used, the length may be as short as 10 or 11 nucleotides. If PCT primers are being used, they are generally 16 to 24 nucleotides long.

The test strip materials preferably filter and/or retain particulate matter as well as cell debris, the precipitates, etc. in the membranes. In addition, since the volume of the sample is preferably so small, the sample stays put in the materials and the elution buffer flowing directly underneath (and through) the sample contacts and transports the sample such that the sample may be extracted, lysed, and/or filtered before it reaches the test line of the detection zone.

In most cases, it is preferable to add a denaturant or lysis agent in situ to the sample in order to make the nucleic acids in the sample accessible to the reagent zone tagged nucleic acids. As discussed herein, the term "lysis agent" is used to describe agents that lyse the cells or otherwise break up the components of the sample, and/or denature the proteins or nucleic acids in the sample. Although the lysis agent may be added to the sample prior to application of the sample to the test strip, the lysis agent is preferably pre-loaded onto a zone of the test strip as a dried denaturant or lysis agent so that the sample may be applied directly to the test strip without a step of adding denaturant or other lysis agent. Alternatively, the lysis agent may be pre-dried by freeze drying or lyophilizing and then pre-loaded into the test strip. The lysis agent can be absorbed, adsorbed, embedded, or trapped on the test strip. The dried or embedded denaturant or lysis agent is pre-loaded onto the test strip in a location so that it frees the target nucleic acids to complex with the mobile tagged nucleic acid reagents on the test strip. The dried or embedded denaturant or lysis agent is preferably soluble in the transport liquid and located in the sample application zone or between the sample application zone and the zone where the nucleic acid reagents are pre-loaded. In other embodiments, mild lysis agents may be part of the running buffer. In this scenario, there is no adverse effect on the reagent zone (containing the mobile tagged nucleic acid reagents) and the sample may be applied upstream, downstream, or overlapping the reagent zone. In other embodiments, commercially available media, for example Whatman FTA cards (Whatman, Kent, UK), can be used separately or incorporated into the test strip.

If the sample that has been collected is not lysed prior to collection and transfer to the sample analysis device, the number of steps needed to collect and prepare the sample for analysis is decreased. In these embodiments, following sample loading, the sample traveling with the transport liquid (buffer) will encounter a lysis agent. In embodiments testing for double stranded nucleic acid targets, the lysis agent includes a denaturant, which denatures the nucleic acid into single strands accessible to the mobile tagged nucleic acid. The lysis agent will have preferably been pre-loaded and dried onto the test strip and is eluted by the transport liquid. The initially dried lysis agent is preferably localized in the sample application zone, but may alternatively be located between the sample application zone and a reagent zone or overlapping either or both of these zones. The lysis agent is preferably soluble in the sample transport liquid, and the lysis agent is solubilized and activated upon contact with the sample transport liquid. The sample transport liquid then contains both lysis agent in solution or suspension and sample components in suspension. Any lysis-susceptible or denaturant-susceptible components in a sample, then being exposed in suspension to the lysis agent, are themselves lysed and denatured in situ. The running buffer then carries the analyte, including any lysis-freed components, to a detection zone.

The location where the lysis agent is pre-loaded and dried (or embedded) can be varied as needed. In order to maximize the time that the sample has to interact with the lysis agent as well as to minimize the amount of lysis agent reaching the detection zone, the lysis agent may be located in or just downstream of the sample application zone. Alternatively, in order to minimize the distance along which the lysis product must travel before reaching the reagent zone, the lysis agent may be located closer to the reagent zone. In embodiments where the reagent zone is upstream of the sample application zone, the lysis agent is preferably located upstream of the sample application zone or in the sample application zone, such that the sample has been effectively lysed and/or denatured when it encounters the tagged nucleic acid reagents from the reagent zone. In other embodiments, the lysis agent is pre-loaded onto the sample collector device.

U.S. Published Patent Application Nos. 2007/0059682 and 2010/0112725, incorporated herein by reference, disclose detecting an analyte and a sample which can also contain one or more interfering substances. These publications teach separating the analyte from the interfering substances by capturing the interfering substances on the chromatographic carrier, and detecting the analyte on the carrier separated from the interfering substances.

U.S. Pat. No. 7,723,124, incorporated herein by reference, discloses a method for detecting targets, such as pathogens and/or allergy-associated components, in a human body fluid where the body fluid sample is collected by a collection device, such as a swab member. The samples are transferred from the swab member to a sample analysis device, on which an analysis of the targets can occur by immunochemical or enzymatic means. The test result is capable of being displayed within a very short period of time and can be directly read by the user. This enables point-of-care testing with results available during a patient visit. The inventions disclosed in this patent are particularly advantageous for the diagnosis of conjunctivitis.

FIG. 1 shows a schematic top view of a test strip for a lateral flow binding assay for nucleic acid detection in an embodiment of the present invention.

The test strip 10 in this example includes a first section 12, a second section 14, a third section 16, and optionally a fourth section 18. These sections are preferably mounted on a backing material 20. Flow 22 occurs in the left to right direction in the figures. The fourth section 18 serves as an optional waste pad for collecting the transport liquid and materials flowing past the third section 16, also termed the detection zone herein, which preferably includes a nitrocellulose membrane.

Mobile tagged single stranded nucleic acids complementary to the target nucleic acid sequence, for example a cocktail of nucleic acid sequences, are pre-loaded onto a reagent zone. The mobile tagged single stranded nucleic acids are not labeled by a dye or other label that is detectable, for example a dye that is able to be viewed by the naked eye or by fluorescence. In preferred embodiments, the tagged nucleic acid sequences are a plurality of PNA sequences. In some embodiments, the tag is a biotin tag. In other embodiments, the tag is an avidin tag. The reagent zone, where the tagged nucleic acids are preferably pre-loaded, may be located in the first section 12, the second section 14, or the third section 16 of the test strip 10. The sample application zone, where the sample is applied to the test strip, is preferably located in the second section 14. When the reagent zone is located in the first section 12, the reagent zone is therefore located upstream of the sample application zone. When the reagent zone is located in the second section 14, the reagent zone preferably overlaps the sample application zone. When the reagent zone is located in the third section 16, the reagent zone is located downstream of the sample application zone and upstream of the detection zone. Lysis agents and/or denaturants are also preloaded onto the test strip. In some embodiments, the lysis zone, which includes the lysis agents and/or denaturants, is located in the second section 14, and the lysis zone overlaps the sample application zone. In other embodiments, the lysis zone is located in the third section 16, downstream of the sample application zone but upstream of the detection zone or in the third section 12, upstream of the sample application zone. In embodiments where the reagent zone is located in the first section 12, upstream of the sample application zone, the mobile tagged nucleic acids need to encounter the sample at some point during or after the sample is lysed and denatured, so that the mobile tagged nucleic acids are able to access and bind to the target nucleic acid sequences.

Figure 3:
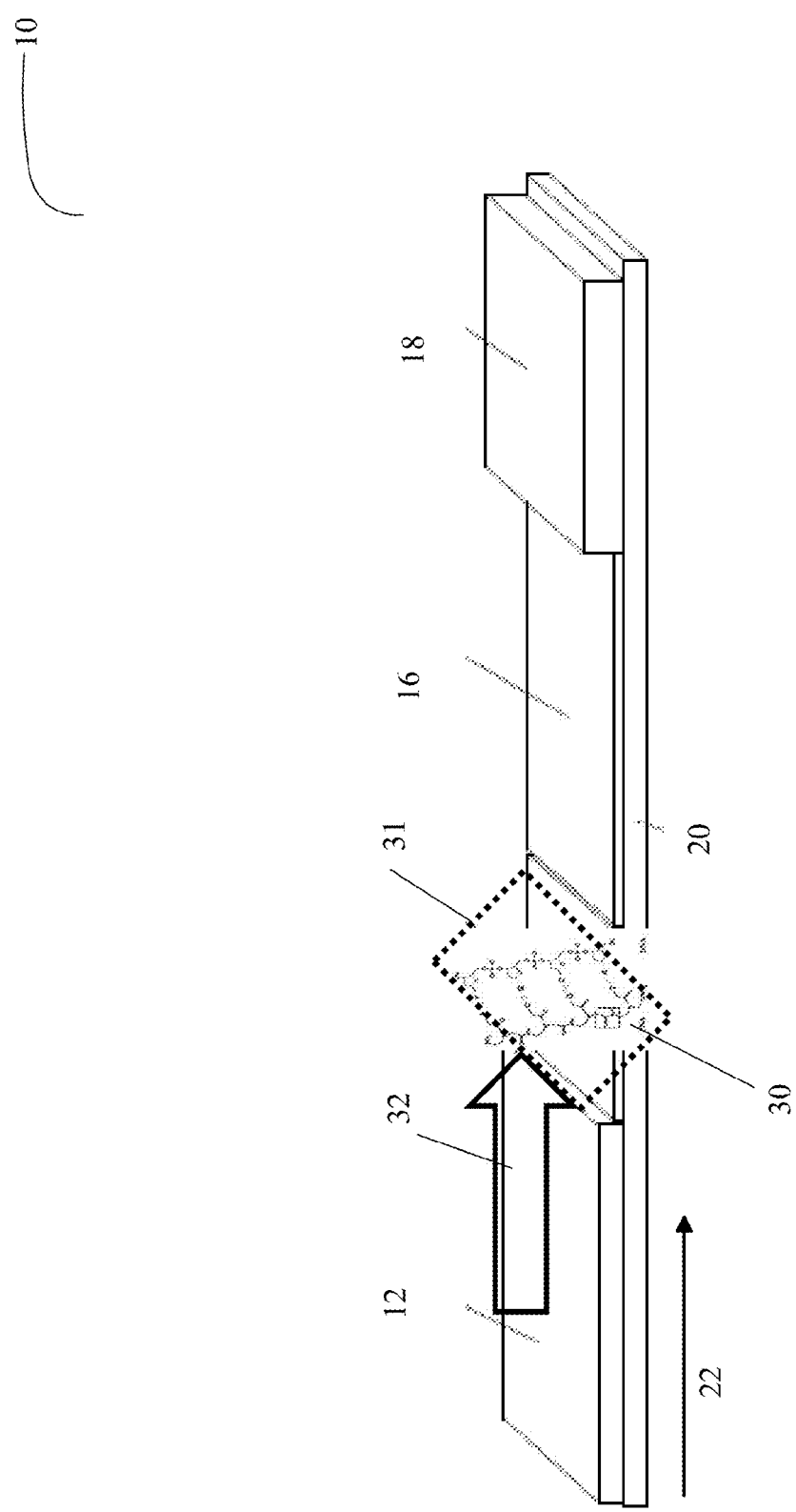
FIG. 3 schematically shows a running buffer added to the test strip of FIG. 1 in an embodiment of the present invention.

The first section 12 is preferably an absorbent pad onto which the running buffer 19 is added, as shown in FIG. 3. However, the first section 12 is optional in embodiments where neither the reagent zone nor the lysis zone is upstream of the sample application zone.

The running buffer preferably includes one or more dyes or labels that bind to double stranded nucleic acids. Any label that binds to any double stranded nucleic acid and is detectable could be used in the running buffer of the present invention. In other embodiments, the dye or label may be located on the test strip prior to use, in a location where it will encounter the sample and the other reagents before they reach the test zone. In still other embodiments, the dye or label can be added to the test strip separately from the running buffer.

In preferred embodiments, the label is visible by the naked eye and/or by fluorescence. In a preferred embodiment, the dye is a dye that binds only double stranded DNA, for example the dyes disclosed in U.S. Pat. Nos. 5,312,921, 5,763,162, 5,783,687, and 6,054,272, herein incorporated by reference, including, but not limited to, thiazole orange tetramethylpropane diamine, thiazole orange tetramethyl diamine, ethidium propane diamine, ethidium diethylene triamine, N,N'-tetramethyl-1,3-diaminopropane)propyl-TAB, Triethylaminobutyl-thiazole blue. and the asymmetric cyanine dye, thiazole orange (4-[3-methyl-2,3-dihydro-(benzo-1,3-thiazole)-2-ethylidene]-quinolinium iodide). One example of a cyanine dye that could be used in the present invention is SYBR® green dye (Life Technologies, Carlsbad, Calif.). SYBR® green dye binds to double-stranded DNA, and upon excitation, emits light. The DNA-dye-complex formed with SYBR® green dye and double stranded DNA absorbs blue light and emits green light. In other embodiments, ethidium bromide dye may be used. In other embodiments, PicoGreen® reagents (Life Technologies, Carlsbad, Calif.) may be used.

The third section 16 preferably includes a detection zone, which is preferably downstream of the reagent zone, the sample application zone, and the lysis zone. The detection zone includes a test zone including one or more test lines, each test line including an immobilized tag, which binds to the tag on the mobile tagged nucleic acids from the reagent zone. In embodiments where biotin is the tag on the mobile tagged nucleic acids, the tag on the immobilized tag in the test zone is preferably avidin, neutrAvidin, or streptavidin. Alternatively, the tag on the mobile nucleic acids may be a lectin and the immobilized tag may be a glycosyl moiety. For example, in some embodiments, the lectin is the Garden pea Lectin and the glycosyl moiety is an erythrocyte glycosyl unit. The tag on the mobile nucleic acids and the immobilized tag may be reversed within the spirit of the present invention. For example, avidin may be the tag on the mobile nucleic acids in the reagent zone, with an immobilized biotin tag in the detection zone.

The immobilization of the tag in the detection zone may be direct, where the immobilization is achieved by binding the tag to at least one chemical, or indirect, where the immobilization is achieved by physically trapping the tag with at least one chemical or other moiety. Immobilization methods include, but are not limited to, associating with poly-lysine, coupling to microbeads, and incorporating into a hydrogel. The microbeads, such as latex beads, may be immobilized directly or trapped in the pores of a medium such as a nitrocellulose membrane, a nylon, or a polyester. The hydrogel may be immobilized in a suitable medium directly or by a trapping mechanism.

The detection zone also preferably include a control zone that includes an immobilized binding partner, capable of binding with a component of the assay to confirm proper operation of the assay, preferably by visual, fluorescent or another known detection method. Although an assay of the present invention may be run without a control zone, a control zone is preferred for confirming negative test results and for comparison to the detection zone for positive test results. The control zone is preferably downstream of the test zone. However, in other embodiments, the control zone may be located upstream of the test zone. Although only one control line is shown in the figure, multiple control lines may alternatively be used. Any known control system could be used in the present invention.

In a preferred embodiment, the control line in the control zone is preferably made of an immobilized cocktail of double stranded nucleic acids from a species unrelated to the species from which the sample was taken. As an example, when the target is from a human sample, the immobilized nucleic acids may come from chicken or fish. The mobile control moiety is a cocktail of nucleic acids complementary to the immobilized cocktail of nucleic acids. In a preferred embodiment, the mobile control moiety is the tagged single stranded nucleic acids from the reagent zone. Since these mobile single stranded nucleic acids are also complementary to the immobile single stranded nucleic acids at the control line, the two sequences always bind to each other, regardless of whether the test is positive or negative for the target nucleic acid. Thus, the control line mimics the test line. Once bound, the resulting double stranded nucleic acid, which is now immobilized at the test line, binds to the dye (which is preferably always in excess during the assay) and shows a positive result on the control line if the test has run correctly.

In another preferred embodiment, the control zone includes a recombinant protein which binds to a component of the elution medium or other composition being used in the test. In one example, the recombinant protein is a lectin. Lectins are specific binding agents for different proteins. Lectins are complex molecules containing both protein and sugars. Lectins bind to the outside of a cell and can cause biochemical changes in the cell. This family of plant/animal proteins binds very specifically to particular sugar residues of glycoproteins. Different lectins are specific for certain materials, for example, some bind to albumins, while others may bind to red blood cell or white blood cell membranes. Particular lectins can be chosen for use in the present invention based on their affinities for glycoproteins that may be found in the running buffer or other composition being used in the methods and devices of the present invention.

In one preferred embodiment, Albegone recombinant protein, a lectin which binds to all mammalian albumins, may be used. Albegone recombinant protein is a proprietary recombinant protein from Advanced Product Development and Consulting for the Life Sciences, State College, Pa.

Albumins, such as Bovine Serum Albumin (BSA) and the human counterpart HSA are often used in point of care devices in a variety of ways. For example, the albumins may be in the running buffer, to block the unreacted sites on nitrocellulose, in the reagent or sample application zones or in the reagents themselves.

In one preferred embodiment, the sample application zone, which is preferably located in the second section 14 of FIG. 1, is coated with two compositions such that the sample application zone, the reagent zone, and the lysis zone overlap and all three zones are located in the second section 14. The first composition lyses and denatures the target nucleic acid to single strands. The second composition includes a tagged cocktail of nucleic acid sequences, including, but not limited to, Peptide Nucleic Acid sequences selected to bind to the antisense (complementary) portions of the single stranded nucleic acid. The PNAs are preferably tagged with biotin and both the first composition and the second composition are mobile.

Figure 2:
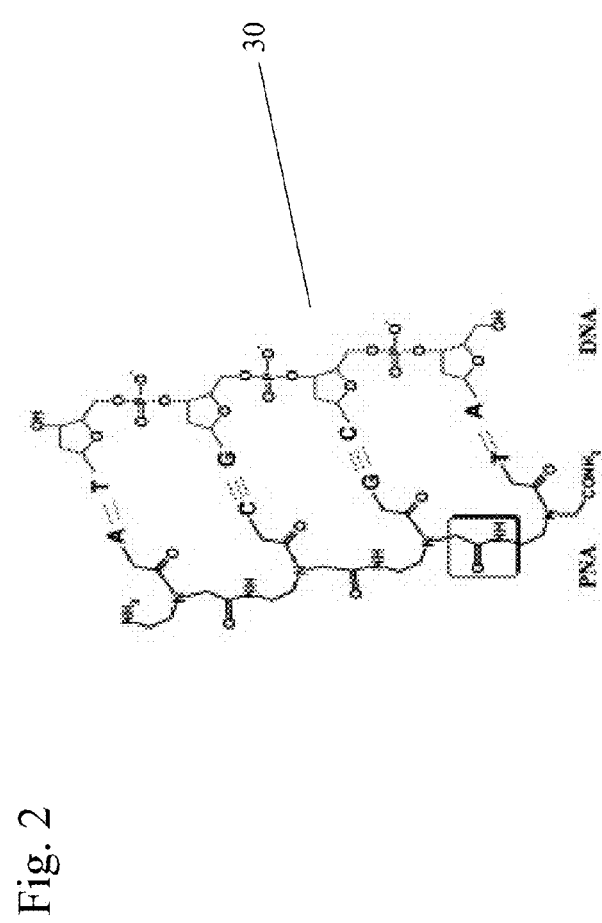
FIG. 2 schematically shows an example of a double stranded PNA-DNA complex.

The lysis/denaturant composition lyses the sample to make the components of the sample accessible to the assay. For double stranded targets, the lysis/denaturant composition also denatures the nucleic acid target into single stranded nucleic acid. A first complex is formed after at least a portion of the sample is transferred to the sample application zone and encounters the PNAs and the single stranded target nucleic acid binds to its complementary PNAs. An example of a PNA-DNA complex 30 is shown in FIG. 2.

As shown in FIG. 3, a running buffer that includes one or more detectable labels that bind to double stranded nucleic acid is added to the test strip. In a preferred embodiment, the label is SYBR® green dye. SYBR® green dye binds to double-stranded DNA, and upon excitation, emits light. The DNA-dye-complex formed with SYBR® green dye and double stranded DNA absorbs blue light and emits green light. In another preferred embodiment, the label is ethidium bromide. As shown by arrow 32, the running buffer travels to the second section 14, where it binds to the double stranded nucleic acid complex formed between the PNAs and the target nucleic acids. The resulting complex (a dyed duplex of nucleic acids) is now dyed and labeled 31 such that it can be detected in the detection zone.

Figure 4:
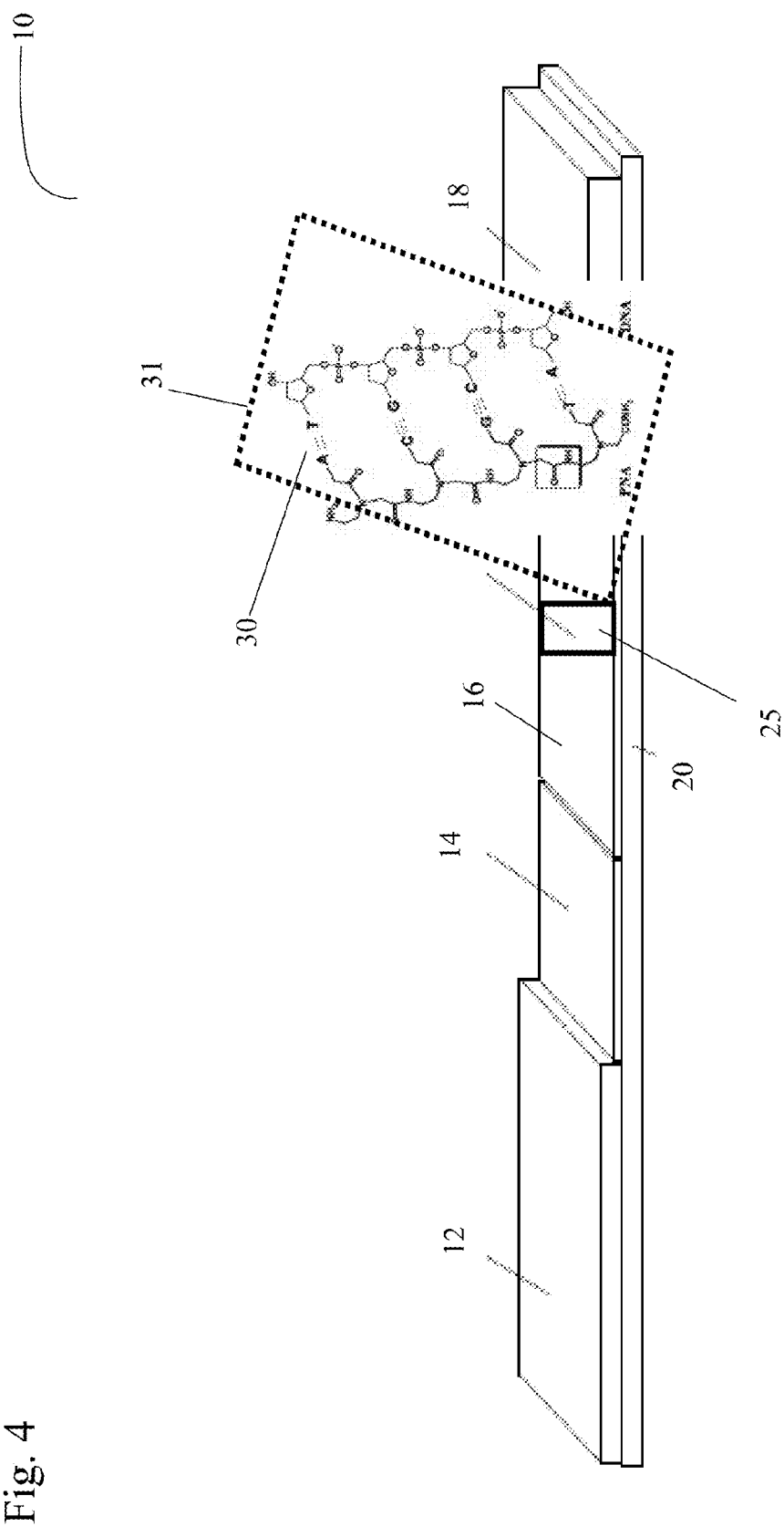
FIG. 4 schematically shows a tagged and labeled nucleic acid complex at the detection zone of the test strip of FIG. 1 in an embodiment of the present invention.

The test zone 25 of the detection zone in FIG. 4 is impregnated with an immobilized tag that binds to the mobile tag on the mobile tagged nucleic acids from the reagent zone to form a complex between the mobile tagged nucleic acids and the immobilized tag. If the target nucleic acid is present, the complex formed between the mobile tag portion of the dyed duplex and the immobilized tag is also dyed and labeled, as shown in FIG. 4. The dyed duplex accumulates at one or more test lines in the test zone 25. The dyes in the running buffer are preferably visible as well as fluorescent. Under their specific excitation wavelength, there is an emission of fluorescence which can be visually observed or "read" by a spectrometer. There are dyes that can become turbid in the presence of certain salts such as magnesium pyrophosphate and one can ascertain the turbidity also at the test line.

While the test strip shown in FIG. 1 has a certain configuration, other configurations with different locations for sample application, the reagent nucleic acid zone, and placement of the denaturant/lysis agent are within the spirit of the present invention. Some examples of other designs are shown in FIGS. 5-14.

Figure 5:
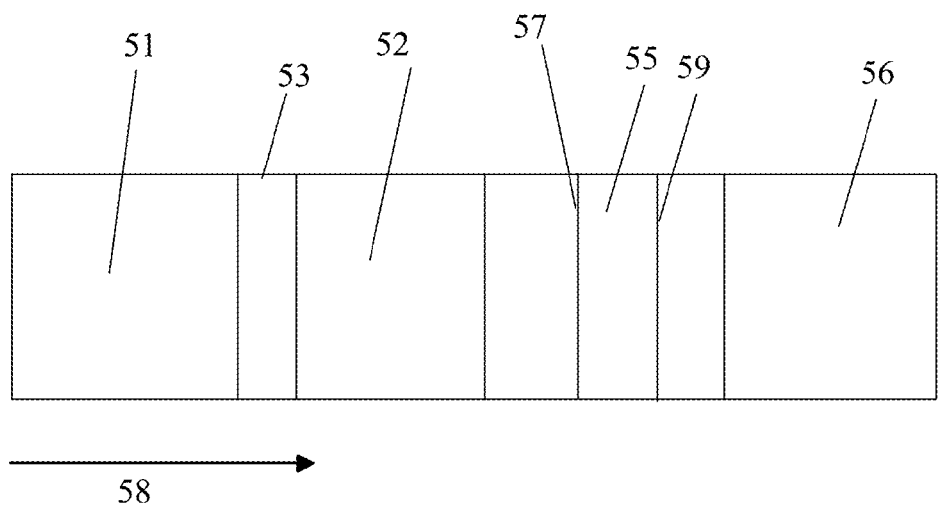
FIG. 5 shows a schematic top view of a test strip for a lateral flow binding assay in an embodiment of the present invention.

FIG. 5 shows a reagent zone 53 upstream of a sample application zone 52 in an embodiment of the present invention. In this embodiment, the mobile tagged nucleic acid reagents are pre-loaded onto the reagent zone 53. The mobile tagged nucleic acid reagents are complementary to a single stranded moiety of the target nucleic acid. In this embodiment, the mobile tagged nucleic acids travel from the reagent zone 53 through the combination sample application and lysis zone 52, which preferably includes lysis agents and/or denaturants. The running buffer, which includes the label that nonspecifically binds to the double stranded nucleic acids formed when the mobile tagged nucleic acids from the reagent zone 53 bind to the single stranded moiety of the target nucleic acid, is preferably added to an absorbent pad 51 upstream of the other elements. One or more test lines 57 in the detection zone 55 include an immobile tag that binds to the mobile tagged nucleic acids. There are also optionally one or more control lines 59 that indicate operability of the test, as well as a waste zone 56 downstream of all of the zones in this figure. Flow 58 occurs in the direction of the arrow.

Figure 6:
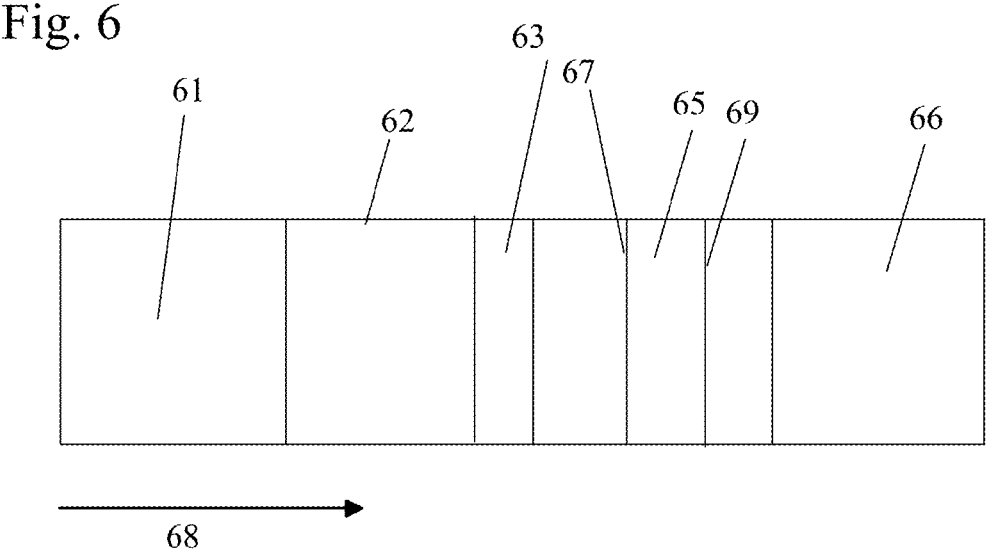
FIG. 6 shows a schematic top view of a test strip for a lateral flow binding assay in another embodiment of the present invention.

FIG. 6 shows a reagent zone 63 downstream of a combination sample application and lysis zone 62 in another embodiment of the present invention. In this embodiment, the mobile tagged nucleic acid reagents are pre-loaded onto the reagent zone 63. The mobile tagged nucleic acid reagents are complementary to a single-stranded moiety of the target nucleic acid. In this embodiment, the sample travels from the sample application and lysis zone 62, which preferably includes lysis agents and/or denaturants. The running buffer, which includes a label that nonspecifically binds to double stranded nucleic acid, is preferably added to an absorbent pad 61 upstream of the other elements. The label binds to the double stranded nucleic acids formed when the mobile tagged nucleic acids from the reagent zone 63 bind to the single stranded moiety of the target nucleic acid. One or more test lines 67 in the detection zone 65 include an immobile tag that binds to the mobile tagged nucleic acids. There are also optionally one or more control lines 69 that indicate operability of the test, as well as a waste zone 66 downstream of all of the zones in this figure. Flow 68 occurs in the direction of the arrow.

Figure 7:
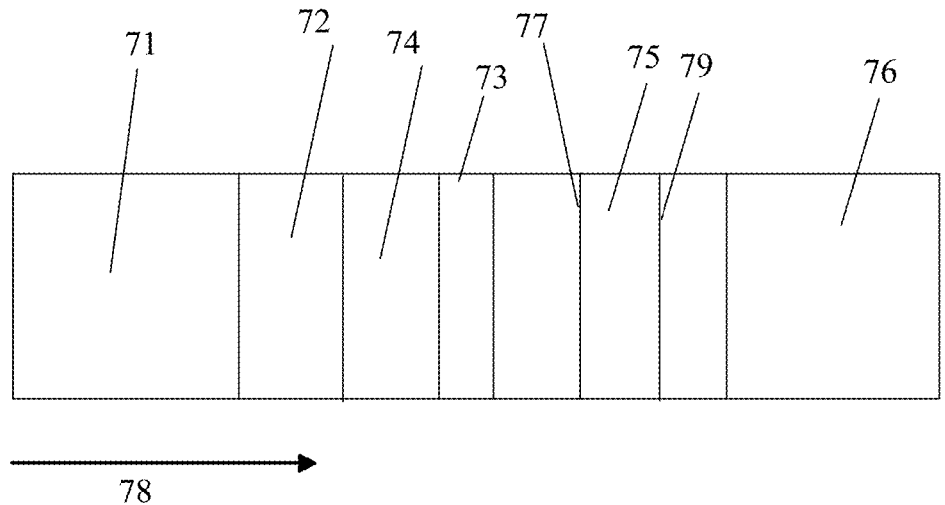
FIG. 7 shows a schematic top view of a test strip for a lateral flow binding assay in another embodiment of the present invention.

FIG. 7 shows a reagent zone 73 downstream of both a sample application zone 72 and a lysis zone 74 in another embodiment of the present invention. In this embodiment, the mobile tagged nucleic acid reagents are pre-loaded onto the reagent zone 73. The mobile tagged nucleic acid reagents are complementary to a single-stranded moiety of the target nucleic acid. In this embodiment, the sample travels from the sample application zone 72, through the lysis zone 74, which preferably includes lysis agents and/or denaturants, and the reagent zone 73. The running buffer, which includes a label that nonspecifically binds to double stranded nucleic acid, is preferably added to an absorbent pad 71 upstream of the other elements. The label binds to the double stranded nucleic acids formed when the mobile tagged nucleic acids from the reagent zone 73 bind to the single stranded moiety of the target nucleic acid. One or more test lines 77 in the detection zone 75 include an immobile tag that binds to the mobile tagged nucleic acids. There are also optionally one or more control lines 79 that indicate operability of the test, as well as a waste zone 76 downstream of all of the zones in this figure. Flow 78 occurs in the direction of the arrow.

Figure 8:
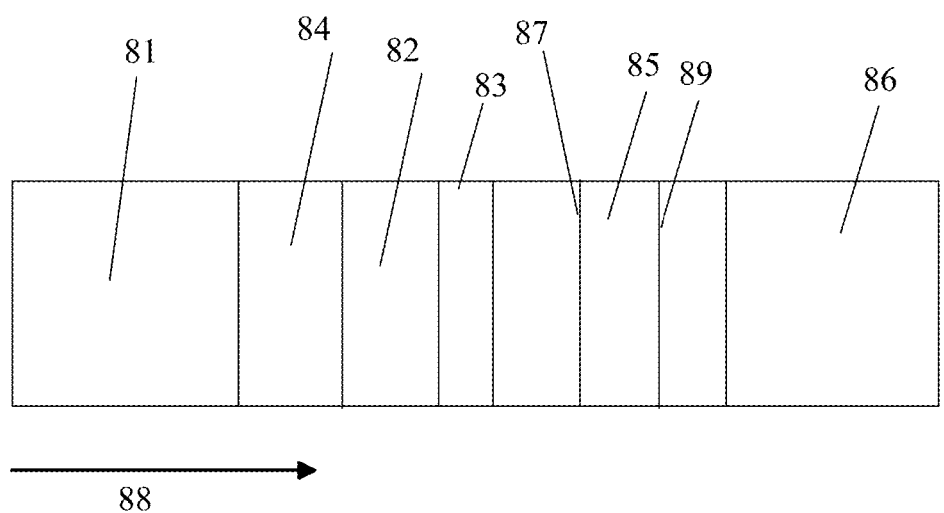
FIG. 8 shows a schematic top view of a test strip for a lateral flow binding assay in another embodiment of the present invention.

FIG. 8 shows a reagent zone 83 downstream of both a sample application zone 82 and a lysis zone 84 in another embodiment of the present invention. In this embodiment, the mobile tagged nucleic acid reagents are pre-loaded onto the reagent zone 83. The mobile tagged nucleic acid reagents are complementary to a single-stranded moiety of the target nucleic acid. In this embodiment, the mobile lysis/denaturing agents travel from the lysis zone 84 to the sample, which is applied to the test strip in the sample application zone 82. The lysed and denatured sample then travels to the reagent zone 83. The running buffer, which includes a label that nonspecifically binds to double stranded nucleic acid, is preferably added to an absorbent pad 81 upstream of the other elements. The label binds to the double stranded nucleic acids formed when the mobile tagged nucleic acids from the reagent zone 83 bind to the single stranded moiety of the target nucleic acid. One or more test lines 87 in the detection zone 85 include an immobile tag that binds to the mobile tagged nucleic acids. There are also optionally one or more control lines 89 that indicate operability of the test, as well as a waste zone 86 downstream of all of the zones in this figure. Flow 88 occurs in the direction of the arrow.

Figure 9:
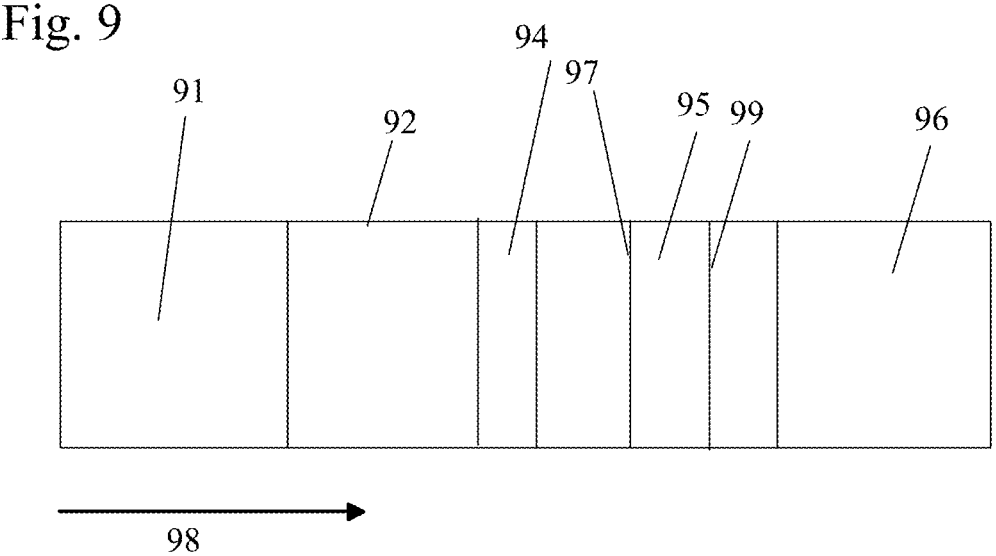
FIG. 9 shows a schematic top view of a test strip for a lateral flow binding assay in another embodiment of the present invention.

FIG. 9 shows a lysis zone 94 downstream of a combination sample application and reagent zone 92 in another embodiment of the present invention. In this embodiment, the mobile tagged nucleic acid reagents are pre-loaded onto the combination sample application and reagent zone 92. The mobile tagged nucleic acid reagents are complementary to a single stranded moiety of the target nucleic acid. The sample and the mobile tagged nucleic acid reagents travel from the combination sample application and reagent zone 92 to the downstream lysis zone 94, where the sample is lysed and denatured and the target nucleic acid binds to the mobile tagged nucleic acid. The running buffer, which includes a label that nonspecifically binds to double stranded nucleic acid, is preferably added to an absorbent pad 91 upstream of the other elements. The label binds to the double stranded nucleic acids formed when the mobile tagged nucleic acids from the reagent zone 92 bind to the single stranded moiety of the target nucleic acid. One or more test lines 97 in the detection zone 95 include an immobile tag that binds to the mobile tagged nucleic acids. There are also optionally one or more control lines 99 that indicate operability of the test, as well as a waste zone 96 downstream of all of the zones in this figure. Flow 98 occurs in the direction of the arrow.

Figure 10:
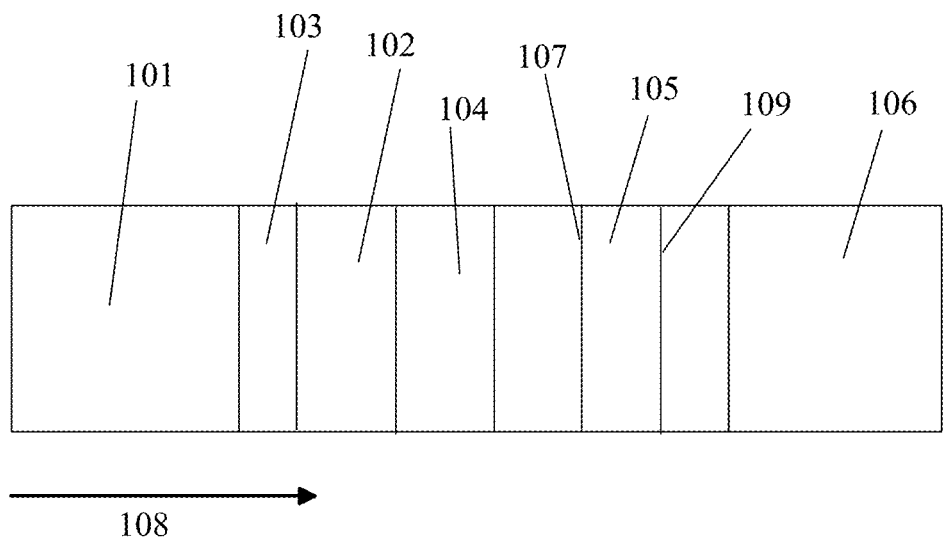
FIG. 10 shows a schematic top view of a test strip for a lateral flow binding assay in another embodiment of the present invention.

FIG. 10 shows a lysis zone 104 downstream of a reagent zone 103 and a sample application zone 102 in another embodiment of the present invention. In this embodiment, the mobile tagged nucleic acid reagents are pre-loaded onto the reagent zone 103. The mobile tagged nucleic acid reagents are complementary to a single-stranded moiety of the target nucleic acid. The reagent zone 103 is upstream of the sample application zone in this embodiment. The sample and the mobile tagged nucleic acid reagents travel downstream to the lysis zone 104, where the sample is lysed and denatured and the target nucleic acid binds to the mobile tagged nucleic acids. The running buffer, which includes a label that nonspecifically binds to double stranded nucleic acid, is preferably added to an absorbent pad 101 upstream of the other elements. The label binds to the double stranded nucleic acids formed when the mobile tagged nucleic acids from the reagent zone 103 bind to the single stranded moiety of the target nucleic acid. One or more test lines 107 in the detection zone 105 include an immobile tag that binds to the mobile tagged nucleic acids. There are also optionally one or more control lines 109 that indicate operability of the test, as well as a waste zone 106 downstream of all of the zones in this figure. Flow 108 occurs in the direction of the arrow.

Figure 11:
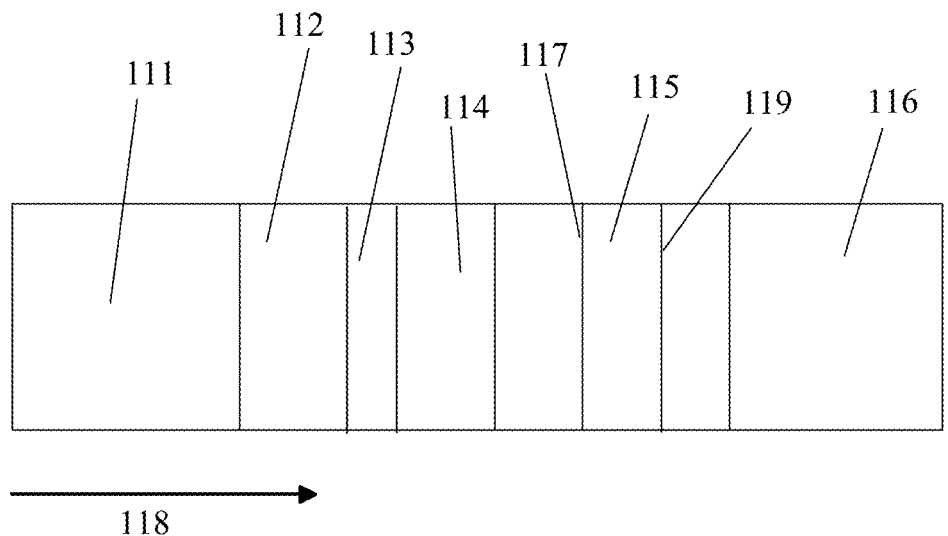
FIG. 11 shows a schematic top view of a test strip for a lateral flow binding assay in another embodiment of the present invention.

FIG. 11 shows a lysis zone 114 downstream of a sample application zone 112 and a reagent zone 113 in another embodiment of the present invention. In this embodiment, the mobile tagged nucleic acid reagents are pre-loaded onto the reagent zone 113. The mobile tagged nucleic acid reagents are complementary to a single-stranded moiety of the target nucleic acid. The reagent zone 113 is downstream of the sample application zone 112 in this embodiment. The sample and the mobile tagged nucleic acid reagents travel downstream to the lysis zone 114, where the sample is lysed and denatured and the target nucleic acid binds to the mobile tagged nucleic acids. The running buffer, which includes a label that nonspecifically binds to double stranded nucleic acid, is preferably added to an absorbent pad 111 upstream of the other elements. The label binds to the double stranded nucleic acids formed when the mobile tagged nucleic acids from the reagent zone 113 bind to the single stranded moiety of the target nucleic acid. One or more test lines 117 in the detection zone 115 include an immobile tag that binds to the mobile tagged nucleic acids. There are also optionally one or more control lines 119 that indicate operability of the test, as well as a waste zone 116 downstream of all of the zones in this figure. Flow 118 occurs in the direction of the arrow.

The tagged nucleic acid reagents in the reagent zone are preferably not affected by the lysis agents. In fact, in preferred embodiments, the lysis agents stabilize single stranded nucleic acids (which include single stranded nucleic acids in the sample or the reagent, as well as single stranded moieties of double stranded target nucleic acid sequences). In preferred embodiments, excess amounts of the label and lysis agents are both included in the assay.

Figure 12:
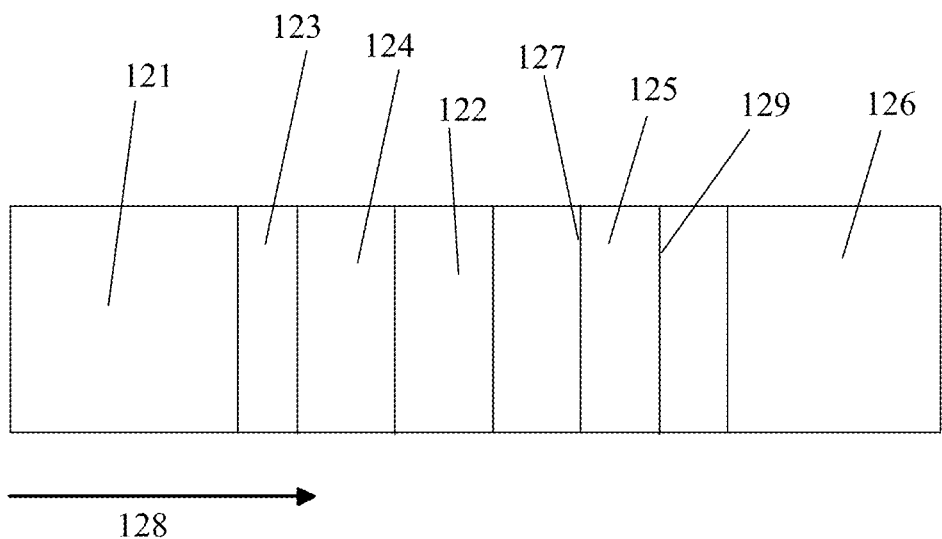
FIG. 12 shows a schematic top view of a test strip for a lateral flow binding assay in another embodiment of the present invention.

FIG. 12 shows a lysis zone 124 upstream of a sample application zone 122 but downstream of a reagent zone 123 in another embodiment of the present invention. In this embodiment, the mobile tagged nucleic acid reagents are pre-loaded onto the reagent zone 123. The mobile tagged nucleic acid reagents are complementary to a single-stranded moiety of the target nucleic acid. The reagent zone 123 is upstream of both the lysis zone 124 and the sample application zone in this embodiment. The mobile tagged nucleic acid reagents and the lysis/denaturing agents travel downstream to the sample application zone 122, where the sample is lysed and denatured and the target nucleic acid binds to the mobile tagged nucleic acid. The running buffer, which includes a label that nonspecifically binds to double stranded nucleic acid, is preferably added to an absorbent pad 121 upstream of the other elements. The label binds to the double stranded nucleic acids formed when the mobile tagged nucleic acids from the reagent zone 123 bind to the single stranded moiety of the target nucleic acid. One or more test lines 127 in the detection zone 125 include an immobile tag that binds to the mobile tagged nucleic acids. There are also optionally one or more control lines 129 that indicate operability of the test, as well as a waste zone 126 downstream of all of the zones in this figure. Flow 128 occurs in the direction of the arrow.

Figure 13:
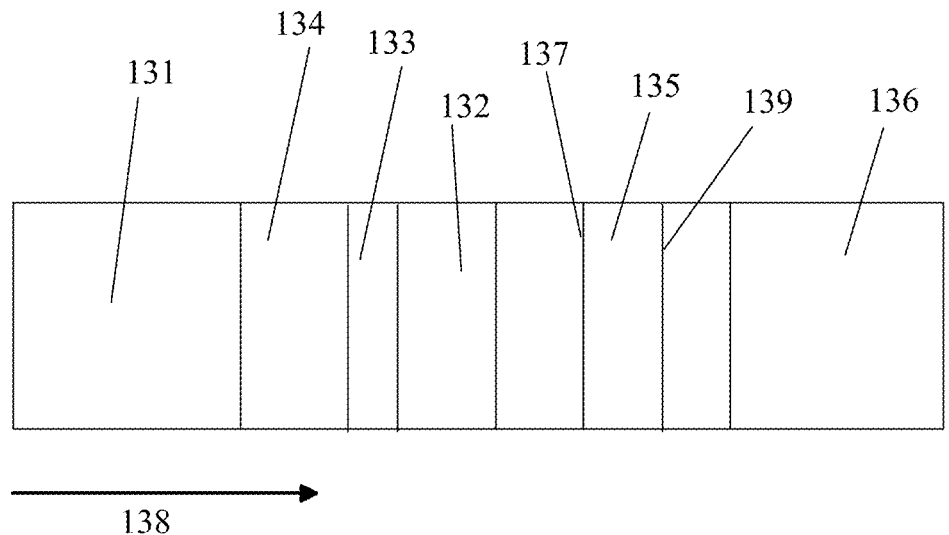
FIG. 13 shows a schematic top view of a test strip for a lateral flow binding assay in another embodiment of the present invention.

FIG. 13 shows a lysis zone 134 upstream of both a sample application zone 132 and a reagent zone 133 in an embodiment of the present invention. In this embodiment, the mobile tagged nucleic acid reagents are pre-loaded onto the reagent zone 133. The mobile tagged nucleic acid reagents are complementary to a single-stranded moiety of the target nucleic acid. The reagent zone 133 is upstream of the sample application zone 132 in this embodiment. The mobile tagged nucleic acid reagents and the lysis/denaturing agents travel downstream to the sample application zone 132, where the sample is lysed and denatured and the target nucleic acid binds to the mobile tagged nucleic acid. The running buffer, which includes a label that nonspecifically binds to double stranded nucleic acid, is preferably added to an absorbent pad 131 upstream of the other elements. The label binds to the double stranded nucleic acids formed when the mobile tagged nucleic acids from the reagent zone 133 bind to the single stranded moiety of the target nucleic acid. One or more test lines 137 in the detection zone 135 include an immobile tag that binds to the mobile tagged nucleic acids. There are also optionally one or more control lines 139 that indicate operability of the test, as well as a waste zone 136 downstream of all of the zones in this figure. Flow 138 occurs in the direction of the arrow.

Figure 14:
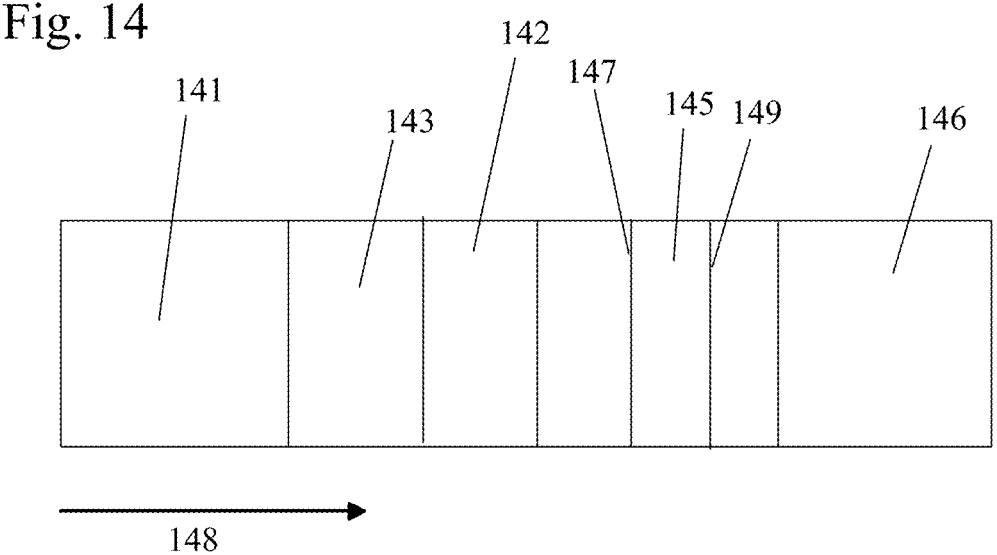
FIG. 14 shows a schematic top view of a test strip for a lateral flow binding assay in another embodiment of the present invention.

FIG. 14 shows a sample application zone 142 downstream of a combination reagent and lysis zone 143 in an embodiment of the present invention. In this embodiment, the mobile tagged nucleic acid reagents are pre-loaded onto the reagent zone 143. The mobile tagged nucleic acid reagents are complementary to a single-stranded moiety of the target nucleic acid. In this embodiment, lysis/denaturing reagents and the mobile tagged nucleic acids travel from the combination reagent and lysis zone 143 to the sample application zone 142. The running buffer, which includes a label that nonspecifically binds to double stranded nucleic acid, is preferably added to an absorbent pad 61 upstream of the other elements. The label binds to the double stranded nucleic acids formed when the mobile tagged nucleic acids from the combination reagent and lysis zone 143 bind to the single stranded moiety of the nucleic acid. One or more test lines 147 in the detection zone 145 include an immobile tag that binds to the mobile tagged nucleic acids. There are also optionally one or more control lines 149 that indicate operability of the test, as well as a waste zone 66 downstream of all of the zones in this figure. Flow 148 occurs in the direction of the arrow.

In the embodiments of FIGS. 5 and 9-14, it is essential that the sample and the reagents in the reagent zone and the lysis zone travel on the membranes on the test strip with a speed that ensures that the sample encounters the reagent zone reagents during or after the sample has been lysed (and the target nucleic acid denatured, if necessary).

Although only one test line is shown in the figures, multiple test lines are within the spirit of the invention. In some embodiments where there are multiple targets, the presence of each target preferably corresponds to a separate test line. In embodiments testing for two target nucleic acids, for example, there is preferably a first mobile tagged nucleic acid reagent and a second mobile tagged nucleic acid reagent, where the first mobile tagged nucleic acid reagent includes a different tag than the second mobile tagged nucleic acid reagent. The first mobile tagged nucleic acid reagent includes a nucleic acid sequence complementary to a first target nucleic acid and the second mobile tagged nucleic acid reagent includes a nucleic acid complementary to the second target nucleic acid. The label in the running buffer nonspecifically binds to double stranded nucleic acid. A first immobilized tag on a first test line in the detection zone binds to the first mobile tagged nucleic acid reagent and a second immobilized tag on a second test line in the detection zone binds to the second mobile tagged nucleic acid reagent. As an example of using two separate tags and their binding partners, the first mobile tagged nucleic acid reagent is preferably tagged with biotin and the first immobilized tag is preferably tagged with avidin, streptavidin or neutravidin. In this example, the second mobile tagged nucleic acid reagent is preferably tagged with a lectin and the second immobilized tag is a glycosyl moiety that specifically binds to the lectin on the second mobile tagged nucleic acid reagent.

In a preferred embodiment, the denaturant or lysis agent is located in the sample application zone such that the nucleic acid is denatured and/or lysed soon after it is added to the test strip. In other embodiments, the denaturant or lysis agent is placed on any location on the test strip such that the target nucleic acid is at least partially denatured and/or lysed prior to or while encountering the mobile tagged nucleic acid reagents.

A "conjugate", as broadly defined, is any combination of two things joined together. The term "labeled conjugate", as it is used in the embodiments discussed below and exemplified in FIGS. 15 and 16, is a reagent that includes a binding partner for an analyte and a detectable label.

In some preferred embodiments, lateral flow test strips include a labeled conjugate, which includes a first binding partner for an analyte and a detectable label, and a second binding partner for the analyte, which includes a tag but not a detectable label. The labeled conjugate and/or the second binding partner may be located upstream of the sample application zone, overlapping the sample application zone, or downstream of the sample application zone in preferred embodiments of the present invention. In other embodiments, the labeled conjugate and/or the second binding partner could be included in the buffer, overlap the detection zone, or even be premixed with the sample prior to application to the test strip. The label of the labeled conjugate is preferably detectable visibly and/or by fluorescence, but any form of detection known in the art may be used, depending upon the label chosen. The detection zone, which is preferably located downstream of the labeled conjugate, the second binding partner, and the sample, includes an immobile tag that binds to the tag portion of the second binding partner. The immobile tag does not bind directly to the analyte; the binding is indirect through an intermediary.

In some embodiments, the detectable label for the labeled conjugate can be colloidal gold, colored latex beads, fluorescent nanoparticles, chemiluminiscent nanoparticles, paramagnetic nanoparticles or phosphorescent nanoparticles.

The visual label may be any label visible to the naked eye, including, but not limited to, colored particles such as colloidal gold, dyed latex beads, selenium, or carbon. In some embodiments, the visual tags are also coated with fluorescing elements. In some embodiments, the fluorescing element is a fluorescing dye. Alternatively, a mixture of preferably colorless fluorescing latex bead conjugates are mixed with colloidal gold (a visible spectrum) conjugates, or conjugates producing a visible read test line, in lateral flow immunoassays to enhance sensitivity of the assay and to aid in visually reading true positives and true negatives. In embodiments where nanoparticles are used, the nanoparticles that may be used include, but are not limited to, selenium, carbon, and colloidal gold.

In one preferred embodiment, the second binding partner is tagged with biotin. In embodiments where the tag on the second binding partner is biotin, the immobilized tag in the detection zone is preferably avidin, neutravidin, or streptavidin. In other embodiments, the second binding partner is tagged with avidin, neutravidin, or streptavidin. In these embodiments, the immobilized tag in the detection zone is preferably biotin. Alternatively, the tag on the second binding partner may be a lectin and the immobilized tag may be a glycosyl moiety. For example, in some embodiments, the lectin is the Garden pea Lectin and the glycosyl moiety is an erythrocyte glycosyl unit. The tag on the second binding partner and the immobilized tag may be reversed within the spirit of the present invention. For example, the glycosyl moiety may be the tag on the second binding partner, with an immobilized lectin tag in the detection zone. In other embodiments, other receptors and ligands may be used.

The embodiments of the present invention provide a sensitive and rapid method for the detection of analytes, e.g. pathogens, immune mediators, nucleic acids (including, but not limited to, nucleic acids coding for pathogens or immune mediators, as well as nucleic acids corresponding to normal or abnormal genetic conditions), and/or low-molecular-weight compounds, including, but not limited to, haptens. The methods and devices are suitable for diagnosis in human beings and animals, e.g. pets or livestock animals. The detection may include direct detection of the analyte and/or the detection of antibodies against the analyte, which are present in the fluid sample to be tested. Preferably, the method includes a parallel determination of a plurality of analytes. The pathogens are preferably selected from viruses or microorganisms, such as bacteria, fungi (e.g. yeast or molds) or parasites (e.g. amoebae or nematodes). The immune mediators are part of the inflammatory cascade and include, but are not limited to, cardiac markers, tumor marks, antibodies, growth factors, complement, cytokines, lymphokines, chemokines, interferons and interferon derivatives, C-reactive protein, calcitonin, amyloid, adhesion molecules, and chemo-attractant components. The low-molecular-weight compounds may include drug molecules or haptens.

In a preferred embodiment, the specific binding partners for the analytes are monoclonal, polyclonal or recombinant antibodies or fragments of antibodies capable of binding to the analyte. In other embodiments, specific binding partners may also be antigens capable of binding to antibodies against the analyte. Other types of binding partners are bioorganic macromolecules like aptamers or receptors, nanoparticles or nucleic acids. The methods and devices of the present invention can be used for any binding assays, and can avoid the use of antibody/antigens or nucleic acids, for example, in ligand-receptor binding assays and enzyme substrate binding assays.

A full "sandwich" is preferably created between the first binding partner of the labeled conjugate, the analyte, and the second binding partner, at the sample application zone when the analyte is present. Alternatively, the full "sandwich" may form between the sample application zone and the detection zone, if either or both of the first binding partner or the second binding partner is located downstream of the sample application zone. The full sandwich then travels to the detection zone, where the tag on the second binding partner binds to the immobilized tag in the detection zone. Note that the complex between the tag on the second binding partner and the immobilized tag in the detection zone occurs regardless of whether or not the analyte is present. However, the complex is only detectable when the analyte is present and the labeled conjugate (which includes a detectable label) has bound to the analyte.

The device also preferably includes a control zone, which indicates whether the test was run correctly. In preferred embodiments, a control zone binding partner, for example a mobile control line binding partner with a visual label, is also located in the sample application zone or elsewhere on the test strip.

FIG. 15a shows a sample analysis device (test strip) 151 and a sample collector 152. The sample collector 152 may be any type of sample collector 152 known in the art, for example the sample collector 152 could be a swab member. The sample 150 may include the analyte 153, as well as interfering particles 155 (which may include interfering proteins or interfering genes) and other interfering particles or cell debris 154. The sample analysis device 151 includes a labeled conjugate zone 158 upstream of the sample application zone 168 in this figure. Although the labeled conjugate zone 158 is shown upstream of the sample application zone 168 in this figure, the labeled conjugate zone 158 may alternatively overlap the sample application zone 168 or be downstream of the sample application zone 168. The sample application zone 168 is also a microfiltration zone, which preferably filters out cell debris and interfering particles 154 that are in the sample 150.

The labeled conjugate zone 158 preferably includes a mobile labeled conjugate 165, which includes a portion 163 that binds to the analyte 153 and a detectable label 169. In some embodiments, the mobile labeled conjugate is a test antibody with a visual label. The detection zone 162 includes a test zone 160 and a control zone 161, which indicates if the test has run smoothly. If the analyte 153 is present in the sample 150, the analyte 153 binds to the labeled conjugate 165, and the labeled conjugate 165-analyte 153 complex travel to the test zone 160 in the detection zone 162, forming a "half" sandwich 172, which is shown in FIG. 15b. The analyte 153 then binds to an immobilized binding partner 167 for the analyte 153, to form the full "sandwich" 175 in a sandwich-type assay. The full sandwich 175 that forms between the portion 163 of the labeled conjugate 165 that binds to the analyte 153, the analyte 153, and the second binding partner 167 when the analyte 153-labeled conjugate 165 complex reach the test zone 160 is shown in FIG. 15c.

The transfer of the sample from the sample collector 152 to the sample application zone 168 on the sample analysis device is preferably a direct transfer and the transfer preferably takes place without pretreatment of the sample on the sample collector 152. In embodiments without pretreatment of the sample or the sample collector 152, pressure 164 is applied and microfiltration occurs in the region where the sample collector fleece directly contacts the fleece on the sample analysis device 151. The fibers of the fleeces interlock to form a grating or physical interference. Thus, larger elements contained in the sample, for example cell debris and interfering particles 154 are held back and not eluted.

The sample application device 151 preferably also includes a blocking zone 159 that includes one or more capturing reagents. This blocking zone captures interfering proteins and/or genes 155 that may be in the sample 150. Capture of an interfering substance 154, 155 by one or more capturing reagents occurs when the capturing reagent interacts in some manner with the interfering substance to keep the interfering substance from interfering with the detection of the analyte. While a blocking zone 159 is shown in FIG. 15, the capturing reagents may be located in a capturing zone 159 made of materials that allow the capturing reagents to be mobile, in the elution medium, mixed and dried with the reagents, incorporated into the sample application zone, incorporated into the sample collector fleece material and/or immobilized on an immobilizing material (for example, nitrocellulose) either as a line or a zone. Any of these or combinations of these may be used in the embodiments of the present invention, depending on the test and sample matrix.

The sample analysis device 151 also optionally includes an absorbent pad 157 upstream of the labeled conjugate zone 158 and the sample application zone 168. Buffer 156 is added and travels in the direction of the arrow to elute the test components, including the sample 150 and the labeled conjugate 165 to the detection zone 162. The sample analysis device 151 also preferably includes a waste pad 176 at the downstream end of the device 151. The sample analysis device 151 may also optionally include a backing 173.

FIG. 16*a* show an example of a test strip in an embodiment of the present invention. The test strip preferably includes an absorbent pad 182, a sample application zone 184, a detection zone 192, and an optional waste pad 187. The test strip also preferably includes a carrier backing 198. Unlike in FIG. 15, in this embodiment, the entire sandwich (first binding partner 163-analyte-153-second binding partner-188) forms in the sample application zone 184. The "full sandwich" 174 is shown in FIG. 16*b*. The test zone 185 in this embodiment includes an immobilized tag 190 that binds to the tag 189 of the second binding partner 188. The immobilized tag 190 does not bind directly to the analyte 153; instead, it binds through an intermediary, the tag 189 on the second binding partner 188 for the analyte 153.

In this embodiment, a first binding partner 163, which is part of the labeled conjugate 165, binds the analyte 153 in the test sample to form half a sandwich. The second binding partner 188 also includes a tag 189. The second binding partner 188 in this embodiment is preferably pre-loaded and dried on the sample application zone 184 of the test strip, while the labeled conjugate 165 is preferably pre-loaded and dried onto a labeled conjugate zone 195 upstream of the sample application zone 184. Alternatively, the second binding partner 188 and/or the labeled conjugate zone 195 may be located anywhere on the test strip upstream of the detection zone including, but not limited to, overlapping the sample application zone, upstream of the sample application zone, or between the sample application zone and the detection zone. In one preferred embodiment, approximately 75-80% of the labeled conjugate 165 is upstream of the sample application zone (with approximately 20-25% of the labeled conjugate 165 overlapping the sample application zone 184) and approximately 75-80% of the second binding partner 188 is located downstream of the sample application zone 184 (with approximately 20-25% of the second binding partner overlapping the sample application zone 184). Although not preferred, in other embodiments, either the labeled conjugate 165, the second binding partner 188, or both may be located in the buffer or pre-mixed with the sample before the sample is added to the test strip. In still other embodiments, any or all of the components could overlap the detection zone.

In some embodiments, both the first binding partner 163 and the second binding partner 188 are different antibodies to the analyte 153. In other embodiments, specific binding partners may also be antigens capable of binding to antibodies against the analyte. Other types of binding partners are bioorganic macromolecules like aptamers or receptors, nanoparticles or nucleic acids. The device shown in FIG. 16*a* can be used for any binding assays, and can avoid the use of antibody/antigens or nucleic acids, for example, in ligand-receptor binding assays and enzyme substrate binding assays.

In one preferred embodiment, the second binding partner 188 is tagged 189 with biotin. In embodiments where the tag 189 on the second binding partner 188 is biotin, the immobilized tag 190 in the detection zone 192 is preferably avidin, neutravidin, or streptavidin. In other embodiments, the second binding partner 188 is tagged 189 with avidin, neutravidin, or streptavidin. In these embodiments, the immobilized tag 190 in the detection zone 192 is preferably biotin. Alternatively, the tag 189 on the second binding partner 188 may be a lectin and the immobilized tag 190 may be a glycosyl moiety. For example, in some embodiments, the lectin is the Garden pea Lectin and the glycosyl moiety is an erythrocyte glycosyl unit. The tag on the second binding partner and the immobilized tag may be reversed within the spirit of the present invention. For example, the glycosyl moiety may be the tag on the second binding partner, with an immobilized lectin tag in the detection zone. In other embodiments, other receptors and ligands may be used for the tags.

In operation, a sample collector containing the sample is placed such that the sample is directly above the sample application zone 184. In preferred embodiments, the sample has not been subject to pretreatment prior to application to the test strip. Instead, the sample is still in its native form.

The sample is transferred to the sample application zone 184 of the test strip. A sandwich forms with the labeled conjugate 165 as one piece of bread and the second binding partner 188 as a second piece of bread, with the analyte 153 in between them, when the three components come into contact with each other during flow 193. The labeled conjugate 165—analyte 153 (if present)—second binding partner 188 complex (a complete sandwich) flow to the detection zone 192. An immobilized tag 190 in the test zone 185 then binds the tag 189. Since the labeled conjugate 165 includes a label 169, the complex that forms is detectable and indicates a positive result. Proper operation of the test also results in a detectable positive result in the control zone 186, preferably due to the interaction between a control line binding partner and its immobilized partner in the control zone 186.

Although it is not shown, there may also optionally be a lysis zone, which preferably overlaps the sample application zone 184 or is alternatively located in other portions of the test strip within the spirit of the present invention. In other embodiments, there may be a blocking zone that includes capturing reagents, similar to the zone discussed with respect to FIG. 15*a*.

Although the methods and devices described in FIG. 16 are sandwich assays, methods and devices in these embodiments may equally be used in competitive assays. In these competitive assays, the labeled conjugate preferably includes an analyte or an analyte analog, instead of a binding partner for the analyte, bound to a detectable label. The labeled conjugate competes with the analyte of interest for the binding sites of the second binding partner, which includes the first tag. A positive test result is then indicated by the lack of the presence of the label in the test zone of the test strip.

In some preferred embodiments using tags, the detection zone, where either the hybridized double stranded nucleic acid (see FIGS. 1-14) or the full sandwich (see FIGS. 15 and 16) bind, includes an antibody against the tag (which is on the mobile nucleic acid reagents in FIGS. 1-14 and on the second binding partner in FIGS. 15 and 16). The antibody may be a monoclonal, polyclonal or single domain antibody. For example, when the tag is biotin, an anti-biotin antibody is immobilized in the test zone instead of avidin, neutravidin, or streptavidin.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A test strip for detection of at least one target nucleic acid in a sample comprising:
    at least one detection zone comprising at least one test zone;
    a sample application zone for applying the sample to the test strip;
    at least one mobile tagged nucleic acid reagent comprising a plurality of nucleic acid sequences complementary to a first portion of a sequence of the target nucleic acid and at least one tag portion comprising a first tag, wherein the mobile tagged nucleic acid reagent does not include a detectable label and wherein the mobile tagged nucleic acid reagent is loaded in a reagent zone;

at least one second immobilized tag that binds to the first tag, wherein the immobilized tag is immobilized in a test zone on the test strip; and a running buffer that includes at least one detectable label, wherein the detectable label is a dye that binds to double stranded nucleic acids; and wherein the sample, the mobile tagged nucleic acid reagent, and the immobilized tag are all loaded on the test strip at locations such that the sample encounters the mobile tagged nucleic acid reagent and the immobilized tag while running an assay to detect the target nucleic acid in the sample.

2. The test strip of claim 1, further comprising at least one lysis agent, wherein the lysis agent is loaded in a lysis zone located such that the lysis agent lyses the sample and a plurality of single strands of the target nucleic acid are accessible to the mobile tagged nucleic acid reagent at some point during the assay when the sample encounters the mobile tagged nucleic acid reagent.

3. The test strip of claim 2, wherein the target nucleic acid is a double-stranded nucleic acid.

4. The test strip of claim 1, wherein the target nucleic acid is a single-stranded nucleic acid.

5. The test strip of claim 1, wherein the detection zone further comprises a control zone located beyond the test zone.

6. The test strip of claim 1, wherein the detectable label is selected from the group consisting of a cyanine dye that nonspecifically binds to double stranded nucleic acids, a fluorescent dye that nonspecifically binds to double stranded nucleic acids and ethidium bromide.

7. The test strip of claim 1, wherein the mobile tagged nucleic acid reagents comprises peptide nucleic acid (PNA) sequences.

8. The test strip of claim 1, wherein the tag and the immobilized tag comprise a pair selected from the group consisting of:
   a) a first biotin tag and a second immobilized tag selected from the group consisting of avidin, neutravidin and streptavidin;
   b) a first tag selected from the group consisting of avidin, neutravidin and streptavidin and a second biotin immobilized tag;
   c) a first lectin tag and a second glycosyl moiety immobilized tag; and
   d) a first glyosyl moiety tag and a second lectin immobilized tag.

9. The test strip of claim 1, further comprising a lysis agent or a denaturant.

10. The test strip of claim 1, wherein the target nucleic acid is not amplified.

11. A test kit for detection of at least one target nucleic acid in a sample comprising:
   a test strip comprising:
      at least one detection zone comprising at least one test zone;
      a sample application zone for applying the sample to the test strip;
      at least one mobile tagged nucleic acid reagent comprising a plurality of nucleic acids complementary to a first portion of a sequence of the target nucleic acid and at least one tag portion but not including a label, wherein the mobile tagged nucleic acid reagent is loaded in a reagent zone;
      at least one lysis agent loaded in a lysis zone wherein the lysis agent processes the sample such that the target nucleic acid can bind to the mobile tagged nucleic acid reagent when the target nucleic acid encounters the mobile tagged nucleic acid reagent;
      at least one immobilized tag that binds to the tag portion of the mobile tagged nucleic acid reagent, wherein the immobilized tag is immobilized in a test zone of an assay; and
   a running buffer that includes at least one detectable label, wherein the detectable label is a dye that binds to double stranded nucleic acids.

12. The test kit of claim 11, wherein the sample, the mobile tagged nucleic acid reagent, the lysis agent and the immobilized tag are all loaded on the test strip at locations such that:
   if the target nucleic acid is present in the sample, the target nucleic acid binds to the mobile tagged nucleic acid reagent to form a double stranded nucleic acid complex;
   the double stranded nucleic acid complex binds to the dye in the running buffer to form a labeled duplex complex; and
   the immobilized tag binds to the tag portion on the mobile tagged nucleic acid reagent of the labeled duplex complex while running an assay to detect the target nucleic acid in the sample.

* * * * *

UNITED STATES PATENT AND TRADEMARK OFFICE
CERTIFICATE OF CORRECTION

| | | |
|---|---|---|
| PATENT NO. | : 9,121,849 B2 | Page 1 of 1 |
| APPLICATION NO. | : 13/790229 | |
| DATED | : September 1, 2015 | |
| INVENTOR(S) | : Babu et al. | |

It is certified that error appears in the above-identified patent and that said Letters Patent is hereby corrected as shown below:

In The Claims

Claim 8 (Column 26, line 3): replace "a first glyosyl moiety tag" with "a first glycosyl moiety tag"

Signed and Sealed this
Twenty-sixth Day of January, 2016

Michelle K. Lee
*Director of the United States Patent and Trademark Office*